United States Patent
Sagata et al.

(10) Patent No.: US 11,866,548 B2
(45) Date of Patent: Jan. 9, 2024

(54) PERFLUOROPOLYETHER COMPOUND, LUBRICANT, AND MAGNETIC DISK

(71) Applicant: Moresco Corporation, Kobe (JP)

(72) Inventors: Ryosuke Sagata, Kobe (JP); Tsuyoshi Shimizu, Kobe (JP)

(73) Assignee: Moresco Corporation, Kobe (JP)

( * ) Notice: Subject to any disclaimer, the term of this patent is extended or adjusted under 35 U.S.C. 154(b) by 0 days.

(21) Appl. No.: 17/629,165

(22) PCT Filed: Jun. 29, 2020

(86) PCT No.: PCT/JP2020/025430
§ 371 (c)(1),
(2) Date: Jan. 21, 2022

(87) PCT Pub. No.: WO2021/019998
PCT Pub. Date: Feb. 4, 2021

(65) Prior Publication Data
US 2022/0267516 A1    Aug. 25, 2022

(30) Foreign Application Priority Data
Jul. 26, 2019 (JP) .................... 2019-138121

(51) Int. Cl.
| | | |
|---|---|---|
| *C08G 65/00* | (2006.01) | |
| *G11B 5/725* | (2006.01) | |
| *C10M 105/54* | (2006.01) | |
| *C10M 107/34* | (2006.01) | |
| *C10M 107/38* | (2006.01) | |
| *G11B 5/82* | (2006.01) | |
| *C10N 40/18* | (2006.01) | |

(52) U.S. Cl.
CPC .......... *C08G 65/007* (2013.01); *C10M 105/54* (2013.01); *C10M 107/34* (2013.01); *C10M 107/38* (2013.01); *G11B 5/7257* (2020.08); *G11B 5/82* (2013.01); *C08G 2650/38* (2013.01); *C08G 2650/48* (2013.01); *C10M 2211/0425* (2013.01); *C10M 2213/043* (2013.01); *C10M 2213/0606* (2013.01); *C10N 2040/18* (2013.01)

(58) Field of Classification Search
None
See application file for complete search history.

(56) References Cited

U.S. PATENT DOCUMENTS

| | | | | |
|---|---|---|---|---|
| 10,510,997 B2 * | 12/2019 | Ichikawa | ............. | H01M 50/124 |
| 11,555,005 B2 * | 1/2023 | Fukumoto | ............ | C08G 59/308 |
| 2008/0176106 A1 * | 7/2008 | Guo | .................... | C10M 111/04 |
| | | | | 428/800 |
| 2010/0239887 A1 | 9/2010 | Kobayashi | | |
| 2012/0127599 A1 | 5/2012 | Shimokawa et al. | | |
| 2012/0148875 A1 | 6/2012 | Hamakubo et al. | | |
| 2014/0147699 A1 | 5/2014 | Kobayashi | | |
| 2016/0055874 A1 | 2/2016 | Shimokawa et al. | | |
| 2016/0068778 A1 * | 3/2016 | Conley | ................. | G11B 5/8408 |
| | | | | 427/127 |
| 2017/0260472 A1 | 9/2017 | Sagata et al. | | |
| 2017/0349760 A1 * | 12/2017 | Friedrich | .............. | C07C 319/12 |
| 2018/0268853 A1 | 9/2018 | Shimokawa et al. | | |
| 2022/0154093 A1 * | 5/2022 | Pathem | ................ | C10M 137/16 |
| 2022/0220406 A1 * | 7/2022 | Pathem | ................ | G11B 5/4826 |
| 2022/0282176 A1 * | 9/2022 | He | ........................... | C08L 71/00 |
| 2022/0290066 A1 * | 9/2022 | He | ......................... | C10M 107/38 |
| 2022/0364008 A1 * | 11/2022 | Pathem | ................ | G11B 5/4826 |

FOREIGN PATENT DOCUMENTS

| | | |
|---|---|---|
| JP | 2012007008 A | 1/2012 |
| JP | 2018503616 A | 2/2018 |
| WO | WO-2009066784 A1 | 5/2009 |
| WO | WO-2010038773 A1 | 4/2010 |
| WO | WO-2016084781 A1 | 6/2016 |

OTHER PUBLICATIONS

Marchon et al. ("Fomblin Multidentate Lubricants for Ultra-low Magnetic Spacing", Intermag, 2006). (Year: 2006).*
International Search Report from corresponding PCT Application No. PCT/JP2020/025430 dated Sep. 24, 2020.
Written Opinion from corresponding PCT Application No. PCT/JP2020/025430 dated Sep. 24, 2020.
Gorbunova, T.I., et al., "Antifrictional properties of fluorine-containing polyol esters," Fluorine Notes, 80: 1-9 (2012).

* cited by examiner

*Primary Examiner* — Kevin M Bernatz
(74) *Attorney, Agent, or Firm* — Harness Dickey & Pierce P.L.C.

(57) ABSTRACT

Provided is a compound with which a lubricant having excellent adhesion to a magnetic disk, particularly to a protective layer can be provided. A perfluoropolyether compound in accordance with one aspect of this invention has a structure in which two perfluoropolyethers are bonded to each other through an aliphatic ether, the aliphatic ether including a carbon atom to which a primary alcohol is bonded.

6 Claims, 8 Drawing Sheets

| Formula Number: | Chemical Formula: |
|---|---|
| Formula (1) | $R^2\text{-}(CF_2)_a\text{-}Rf\text{-}(CF_2)_a\text{CH}_2\text{O-CH}_2\text{CH(OH) CH}_2\text{OCH}_2\text{—}\underset{\underset{CH_2OH}{\|}}{\overset{\overset{R^1}{\|}}{C}}\text{—CH}_2\text{OCH}_2\text{CH(OH)-CH}_2\text{OCH}_2(CF_2)_a\text{-Rf-}(CF_2)_a\text{-}R^3$ ... (1) |
| Formula (2) | $Rf;(OCF_2CF_2)_b(OCF_2CF_2)_c(OCF_2CF_2)_d(OCF_2CF_2CF_2)_e(OCF_2CF(CF_3))_fO$ ... (2) |
| Formula (3) | $R^2\text{-}(CF_2)_a\text{-}Rf\text{-}(CF_2)_a\text{CH}_2\text{O-CH}_2\text{-}\underset{\underset{O(CH_2CH(OH)CH_2O)_xH}{\|}}{\overset{\overset{R^1}{\|}}{C}}\text{-CH}_2\text{-OCH}_2(CF_2)_a\text{-Rf-}(CF_2)_a\text{-}R^3$ ... (3) |

Fig. 3

| Comp. #: | Structural Formula: |
|---|---|
| 1 | HO−...−OCH$_2$CF$_2$O(CF$_2$CF$_2$O)$_x$(CF$_2$O)$_y$CF$_2$CH$_2$O−...−OCH$_2$CF$_2$O(CF$_2$CF$_2$O)$_x$(CF$_2$O)$_y$CF$_2$CH$_2$O−...−OH (with pendant OH groups) |
| 2 | HO−...−OCH$_2$CF$_2$O(CF$_2$CF$_2$O)$_x$(CF$_2$O)$_y$CF$_2$CH$_2$O−...−OCH$_2$CF$_2$O(CF$_2$CF$_2$O)$_x$(CF$_2$O)$_y$CF$_2$CH$_2$O−...−OH (with pendant OH groups) |
| 3 | HO−...−OCH$_2$CF$_2$O(CF$_2$CF$_2$O)$_x$(CF$_2$O)$_y$CF$_2$CH$_2$O−...−OCH$_2$CF$_2$O(CF$_2$CF$_2$O)$_x$(CF$_2$O)$_y$CF$_2$CH$_2$O−...−OH (with pendant OH groups) |

PERFLUOROPOLYETHER COMPOUND, LUBRICANT, AND MAGNETIC DISK

PRIORITY STATEMENT

This application is a national stage application under 35 U.S.C. § 371 of PCT International Application No. PCT/JP2020/025430, which has an international filing date of 29 Jun. 2020 and claims priority under 35 U.S.C. § 119 to Japanese Patent Application No. 2019-138121 filed on 26 Jul. 2019. The contents of each application recited above are incorporated herein by reference in their entirety.

TECHNICAL FIELD

The present invention relates to a perfluoropolyether compound, a lubricant, and a magnetic disk.

BACKGROUND ART

Many of the existing magnetic disks are constituted by: a recording layer disposed on a substrate; a protective layer disposed on the recording layer in order to protect information recorded on the recording layer; and a lubricant layer disposed on the protective layer.

As conventional techniques related to a surface lubricant for a magnetic disk, the techniques disclosed in Patent Literatures 1 to 4 are known, for example. Patent Literatures 1 to 4 disclose various perfluoropolyether compounds.

CITATION LIST

Patent Literature

[Patent Literature 1]
International Publication No. WO 2016/084781
[Patent Literature 2] International Publication No. WO 2010/038773
[Patent Literature 3]
Japanese Patent Application Publication Tokukai No. 2012-7008
[Patent Literature 4]
International Publication No. WO 2009/066784

SUMMARY OF INVENTION

Technical Problem

However, the above-described conventional techniques have room for improvement in terms of bringing the lubricant layer into close contact with the magnetic disk, particularly with the protective layer.

An aspect of the present invention has an object to provide a lubricant having excellent adhesion with respect to a magnetic disk, particularly with respect to a protective layer.

Solution to Problem

The inventor of the present invention conducted diligent research to attain the above object, and found that a perfluoropolyether compound having a certain structure has excellent adhesion and can maintain adhesion between a magnetic disk and a protective layer even while the magnetic disk is rotating at a high speed. On the basis of this finding, the inventor completed the present invention. Specifically, the present invention encompasses the following aspects.

<1> A perfluoropolyether compound having a structure in which two perfluoropolyethers are bonded to each other through an aliphatic ether,
the aliphatic ether including a carbon atom to which a primary alcohol is bonded.
<2> The perfluoropolyether compound described in <1>, wherein the perfluoropolyether compound is represented by formula (1) shown in FIG. 3,
where:
a is an integer of 1 to 5;
$R^1$ is a hydrogen atom, a hydrocarbon group, or a polar group;
$R^2$ and $R^3$ are each independently —F, —$CH_2OH$, —$CH_2OCH_2CH(OH)CH_2OH$, —$CH_2OCH_2CH(OH)CH_2OCH_2CH(OH)CH_2OH$, —$CH_2O(CH_2)_gOH$, —$CH_2OCH_2CH(OH)CH_2OC_{12}H_9O$, —$CH_2OCH_2CH(OH)CH_2OC_{10}H_7$, or $CH_2OCH_2CH(OH)CH_2OC_6H_4$—$R^4$, where g is a real number of 1 to 10, and $R^4$ is a hydrogen atom, a hydroxyl group, a $C_1$-$C_4$ alkoxy group, an amino group, or an amido group; and
Rf is represented by formula (2) shown in FIG. 3,
where:
b and c are each a real number of 0 to 50;
d, e, and f are each a real number of 0 to 30; and
at least one of b, c, d, e, and f is a real number of 1 or more.
<3> The perfluoropolyether compound described in <1>, wherein the perfluoropolyether compound is represented by formula (3) shown in FIG. 3,
where:
a is an integer of 1 to 5 and x is a real number of 1 to 5;
$R^1$ is a hydrogen atom, a hydrocarbon group, or a polar group;
$R^2$ and $R^3$ are each independently —F, —$CH_2OH$, —$CH_2OCH_2CH(OH)CH_2OH$, —$CH_2OCH_2CH(OH)CH_2OCH_2CH(OH)CH_2OH$, —$CH_2O(CH_2)_gOH$, —$CH_2OCH_2CH(OH)CH_2OC_{12}H_9O$, —$CH_2OCH_2CH(OH)CH_2OC_{10}H_7$, or $CH_2OCH_2CH(OH)CH_2OC_6H_4$—$R^4$, where g is a real number of 1 to 10, and $R^4$ is a hydrogen atom, a hydroxyl group, a $C_1$-$C_4$ alkoxy group, an amino group, or an amido group; and
Rf is represented by formula (2) shown in FIG. 3,
where:
b and c are each a real number of 0 to 50;
d, e, and f are each a real number of 0 to 30; and
at least one of b, c, d, e, and f is a real number of 1 or more.
<4> A lubricant including the perfluoropolyether compound described in any one of <1> to <3>.
<5> A magnetic disk including:
a recording layer;
a protective layer disposed on the recording layer; and
a lubricant layer disposed on the protective layer,
the lubricant layer containing the lubricant described in <4>.

Advantageous Effects of Invention

An aspect of the present invention has an object to provide a compound with which a lubricant having excellent adhesion to a magnetic disk, particularly to a protective layer can be provided.

BRIEF DESCRIPTION OF DRAWINGS

FIG. 3 is a table containing chemical formulas (1)-(3).

DESCRIPTION OF EMBODIMENTS

Figure 1:
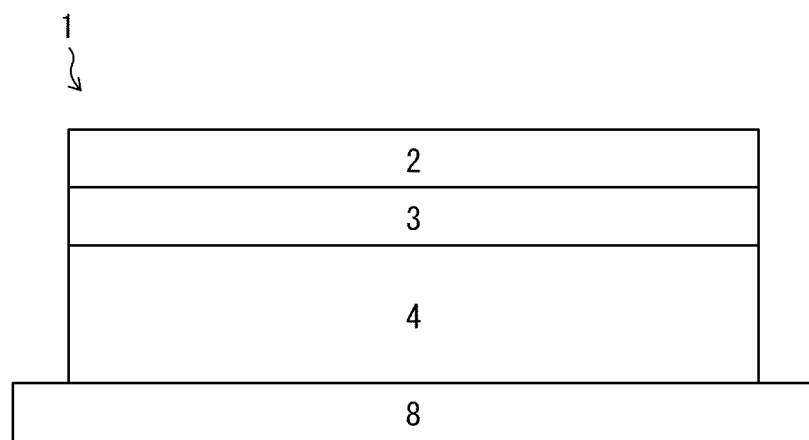
FIG. 1 is a cross-sectional view illustrating a configuration of a magnetic disk in accordance with an embodiment of the present invention.

The following description will discuss embodiments of the present invention in detail. Note, however, that the present invention is not limited to the following embodiments, but can be altered within this disclosure. The present invention also encompasses, in its technical scope, any embodiment derived by combining technical means disclosed in differing embodiments. Note that the expression "A to B", representing a numerical range, herein means "not less than A and not more than B" unless otherwise specified in this specification.

(1. Perfluoropolyether Compound)

A perfluoropolyether compound in accordance with an embodiment of the present invention has a structure in which two perfluoropolyethers are bonded to each other through an aliphatic ether, the aliphatic ether including a carbon atom to which a primary alcohol is bonded.

Examples of the perfluoropolyether encompass a perfluoropolyether having a structure represented by the later-indicated formula (2) shown in FIG. 3.

The aliphatic ether includes a carbon atom to which a primary alcohol is bonded, and has at least one ether linkage, preferably two or more ether linkages in a molecule. In other words, the aliphatic ether has a hydroxyalkyl group corresponding to a primary alcohol. That is, the hydroxyalkyl group has a terminal carbon atom to which a hydroxyl group and two hydrogen atoms are bonded. Examples of such a hydroxyalkyl group encompass a hydroxymethyl group, a hydroxyethyl group, and a hydroxypropyl group.

In order to bring a magnetic disk sufficiently close to a magnetic head, a lubricant between the magnetic disk and the magnetic head is required to have strong adhesion. A lubricant having weak adhesion can rise up along with rotation of the magnetic disk and approach of the magnetic head. This can inhibit approach of the magnetic head. In order to avoid this, there is a need for a lubricant having adhesion so strong as to bring the lubricant layer and the protective layer into close contact with each other to reduce the extend of the rising-up.

Thus, the inventor of the present invention conducted various studies to develop a lubricant having more excellent adherence than that of existing articles. In order to enhance the adherence, increasing the percentage of a polar moiety in a lubricant compound is considered to be effective. As a result of the studies, however, the inventor of the present invention arrived at the following finding. That is, it is not enough just to increase the percentage of the polar moiety, but it is necessary to introduce, into a molecule of the compound, a polar moiety that can be brought into close contact with protective layer more firmly. More specifically, the inventor of the present invention found that a perfluoropolyether compound having a structure in which two perfluoropolyethers are bonded to each other through an aliphatic ether, the aliphatic ether including a carbon atom to which a primary alcohol is bonded has excellent adhesion. A lubricant containing this compound contains the primary alcohol at the center of the perfluoropolyether compound molecule, and therefore has excellent adhesion.

Herein, an evaluation as to whether a lubricant "has excellent adhesion" can be made by evaluating a bonding ratio described in Examples.

A perfluoropolyether compound in accordance with an embodiment of the present invention is represented by formula (1) or (3), as shown in FIG. 3, wherein in formula (1)

a is an integer of 1 to 5;

$R^1$ is a hydrogen atom, a hydrocarbon group, or a polar group;

$R^2$ and $R^3$ are each independently —F, —$CH_2OH$, —$CH_2OCH_2CH(OH)CH_2OH$, —$CH_2OCH_2CH(OH)CH_2OCH_2CH(OH)CH_2OH$, —$CH_2O(CH_2)_gOH$, —$CH_2OCH_2CH(OH)CH_2OC_{12}H_9O$, —$CH_2OCH_2CH(OH)CH_2OC_{10}H_7$, or $CH_2OCH_2CH(OH)CH_2OC_6H_4$—$R^4$, where g is a real number of 1 to 10, and $R^4$ is a hydrogen atom, a hydroxyl group, a $C_1$-$C_4$ alkoxy group, an amino group, or an amido group; and Rf is represented by formula (2) shown in FIG. 3, where:

b and c are each a real number of 0 to 50;

d, e, and f are each a real number of 0 to 30; and at least one of b, c, d, e, and f is a real number of 1 or more; or in formula 3, a is an integer of 1 to 5 and x is a real number of 1 to 5;

$R^1$ is a hydrogen atom, a hydrocarbon group, or a polar group;

$R^2$ and $R^3$ are each independently —F, —$CH_2OH$, —$CH_2OCH_2CH(OH)CH_2OH$, —$CH_2OCH_2CH(OH)CH_2OCH_2CH(OH)CH_2OH$, —$CH_2O(CH_2)_gOH$, —$CH_2OCH_2CH(OH)CH_2OC_{12}H_9O$, —$CH_2OCH_2CH(OH)CH_2OC_{10}H_7$, or $CH_2OCH_2CH(OH)CH_2OC_6H_4$—$R^4$, where g is a real number of 1 to 10, and $R^4$ is a hydrogen atom, a hydroxyl group, a $C_1$-$C_4$ alkoxy group, an amino group, or an amido group, and Rf is represented by formula (2) shown in FIG. 3, where:

b and c are each a real number of 0 to 50;

d, e, and f are each a real number of 0 to 30; and at least one of b, c, d, e, and f is a real number of 1 or more.

The perfluoropolyether compound represented by the formula (1) or (3) shown in FIG. 3 includes any combination of $R^1$ to $R^4$ described above and Rf represented by formula (2) shown in FIG. 3.

Examples of the hydrocarbon group in $R^1$ encompass an aliphatic hydrocarbon group and an aromatic hydrocarbon group. The aliphatic hydrocarbon group may be a saturated aliphatic hydrocarbon group or an unsaturated aliphatic hydrocarbon group. The aliphatic hydrocarbon group may be linear, branched, or cyclic. The hydrocarbon group preferably has 1 to 20 carbon atoms, more preferably 1 to 10 carbon atoms. Examples of the polar group in $R^1$ encompass a hydroxyl group, an amino group, an aldehyde group, a carboxyl group, a thiol group, and a sulfonic acid group. The hydrocarbon group may be partially substituted by a polar group. $R^1$ is preferably —H, —$CH_2CH_3$, —$CH_2CH_2CH_3$, —$CH_2OH$, —$CH_2CH_2OH$, —$CH_2CHCH_2$, —$CH_2CH(CH_3)_2$, —$CH_2C_6H_5$, —$CH_2C_6H_4NO_2$, or —$CH_2C_6H_4NH_2$.

Examples of $R^2$ and $R^3$ encompass —F, —$CH_2OH$, —$CH_2OCH_2CH(OH)CH_2OH$, —$CH_2OCH_2CH(OH)CH_2OCH_2CH(OH)CH_2OH$, —$CH_2O(CH_2)_gOH$, —$CH_2OCH_2CH(OH)CH_2OC_{12}H_9O$, —$CH_2OCH_2CH(OH)CH_2OC_{10}H_7$, —$CH_2OCH_2CH(OH)CH_2OC_6H_4$—$R^4$. $R^2$ and $R^3$ are each preferably —$CH_2OCH_2CH(OH)CH_2OH$, —$CH_2OCH_2CH(OH)CH_2OCH_2CH(OH)CH_2OH$, —CH$_2$OCH$_2$CH(OH)CH$_2$OC$_{12}$H$_9$O, —CH$_2$OCH$_2$CH(OH)CH$_2$OC$_{10}$H$_7$, or —CH$_2$OCH$_2$CH(OH)CH$_2$OC$_6$H$_4$—R$^4$.

Examples of R$^4$ encompass a hydrogen atom, a hydroxyl group, a C$_1$-C$_4$ alkoxy group, an amino group, and an amido group. R$^4$ is preferably a hydroxyl group or an alkoxy group.

Examples of Rf encompass Demnum skeleton (—(CF$_2$CF$_2$CF$_2$O)$_d$—), Fomblin skeleton (—(CF$_2$O)$_b$(CF$_2$CF$_2$O)$_c$—), C2 skeleton (—(CF$_2$CF$_2$O)$_c$—), C$_4$ skeleton (—(CF$_2$CF$_2$CF$_2$O)$_e$—), and Krytox skeleton (—(CF(CF$_3$)CF$_2$O)$_f$—). In these skeletons, b, c, d, e, and f are each a real number of 1 to 15. In Fomblin skeleton, CF$_2$O and CF$_2$CF$_2$O can be randomly repeated.

(2. Method for Producing Perfluoropolyether Compound)

There is no particular limitation on a method in accordance with an embodiment of the present invention for producing a perfluoropolyether compound. The perfluoropolyether compound represented by formula (1), as shown in FIG. 3, can be obtained by, e.g., allowing a linear fluoropolyether compound (a) having, at one terminal thereof, a hydroxyl group and having, at the other terminal thereof, an alkoxy group having a hydroxyl group to react with an alkyl compound (A-1) having an epoxy group.

The alkyl compound (A-1) having the epoxy group constitutes a moiety corresponding to the above-described "aliphatic ether including a carbon atom to which a primary alcohol is bonded". The hydroxyl group at the one terminal of the compound (a) is a moiety that is to be bonded to the aliphatic ether, whereas the alkoxy group that is at the other terminal and that has the hydroxyl group constitutes the terminal of the compound represented by formula (1) shown in FIG. 3, i.e., moieties corresponding to R$^2$ and R$^3$. A compound represented by formula (1), as shown in FIG. 3, wherein R$^2$ and R$^3$ are each —F, —CH$_2$OH, or the like, not an alkoxy group, can be obtained by employing a compound (a) having —F, —CH$_2$OH, or the like at the other terminal thereof.

The perfluoropolyether compound represented by formula (3) shown in FIG. 3 can be obtained by, e.g., allowing a linear fluoropolyether compound (d) having a hydroxyl group in a perfluoropolyether chain to react with glycidol.

<2-1. Synthesis of Linear Fluoropolyether Compound (a) Having, at One Terminal Thereof, Hydroxyl Group and Having, at the Other Terminal Thereof, Alkoxy Group Having Hydroxyl Group>

First, a linear fluoropolyether compound (b) having hydroxyl groups at both terminals is allowed to react with a compound (c) that can react with a hydroxyl group to form an alkoxy group having a hydroxyl group. The reaction temperature is preferably 20° C. to 90° C., more preferably 60° C. to 80° C. The reaction time is preferably 5 hours to 20 hours, more preferably 10 hours to 15 hours. The amount of the compound (c) to be used is preferably an equivalent weight of 0.5 to 1.5 with respect to the compound (b). The reaction may be carried out with use of a reaction accelerator. Examples of the reaction accelerator encompass sodium hydroxide, potassium t-butoxide, sodium t-butoxide, and sodium hydride. The reaction may be carried out in a solvent. Examples of the solvent encompass t-butyl alcohol, dimethyl formaldehyde, 1,4-dioxane, dimethyl sulfoxide, and dimethylacetamide. Then, a product obtained from the reaction is purified by, e.g., column chromatography. This can yield a linear fluoropolyether compound (a) having, at one terminal thereof, a hydroxyl group and having, at the other terminal thereof, an alkoxy group having a hydroxyl group.

A linear fluoropolyether compound (b) having hydroxyl groups at both terminals is represented by HOCH$_2$(CF$_2$)$_a$O (CF$_2$O)$_b$(CF$_2$CF$_2$O)$_c$(CF$_2$CF$_2$CF$_2$O)$_d$(CF$_2$CF$_2$CF$_2$CF$_2$O)$_e$(CF$_2$CF(CF$_3$)O)$_f$(CF$_2$)$_a$CH$_2$OH. Here, a is an integer of 1 to 5, b and c are each a real number of 0 to 50, d, e, and f are each a real number of 0 to 30, and at least one of b, c, d, e, and f is a real number of 1 or more. Specific examples of the linear fluoropolyether compound (b) encompass a compound represented by HOCH$_2$CF$_2$O(CF$_2$O)$_b$(CF$_2$CF$_2$O)$_c$CF$_2$CH$_2$OH, a compound represented by HOCH$_2$CF$_2$O(CF$_2$CF$_2$O)$_c$CF$_2$CH$_2$OH, a compound represented by HOCH$_2$CF$_2$CF$_2$O(CF$_2$CF$_2$CF$_2$O)$_d$CF$_2$CF$_2$CH$_2$OH, and a compound represented by HOCH$_2$CF$_2$CF$_2$O(CF$_2$CF$_2$CF$_2$CF$_2$O)$_e$CF$_2$CF$_2$CF$_2$CH$_2$OH. The number average molecular weight of the linear fluoropolyether compound (b) is typically 200 to 5000, preferably 400 to 1500.

The number average molecular weight is a value determined by $^{19}$F-NMR using JNM-ECX400 available from JEOL Ltd. In the NMR determination, a sample is used as a neat solution without being diluted with a solvent. A known peak that is part of the skeleton structure of the linear fluoropolyether can be used as a reference for the chemical shift.

As described above, a is a real number of 1 to 5. Each of b and c is preferably a real number of 0 to 15, more preferably a real number of 0 to 10. Setting each of b and c so as to be a real number of 0 to 10 provides a flatter molecular chain, and therefore is preferable. Preferably, d is a real number of 1 to 17, more preferably a real number of 1 to 10. Setting d so as to be a real number of 1 to 10 provides a flatter molecular chain, and therefore is preferable. Preferably, e is a real number of 1 to 13, more preferably a real number of 1 to 8. Setting e so as to be a real number of 1 to 8 provides a flatter molecular chain, and therefore is preferable. Preferably, f is a real number of 1 to 16, more preferably a real number of 1 to 10. Setting f so as to be a real number of 1 to 10 provides a flatter molecular chain, and therefore is preferable.

The compound (b) is a compound having a molecular weight distribution, and has a molecular weight distribution (PD) represented by a weight average molecular weight/number average molecular weight of preferably 1.0 to 1.5, more preferably 1.0 to 1.3, even more preferably 1.0 to 1.1. Note that the molecular weight distribution is a property value obtained with use of HPLC-8220GPC available from Tosoh Corporation, a column (PLgel Mixed E) available from Polymer Laboratories, a HCFC-based substitute for CFCs as an eluent, and a non-functional perfluoropolyether as a reference material.

Examples of the compound (c) encompass a compound having an epoxy group, haloalkyl alcohols represented by X(CH$_2$)$_m$OH, and a phenoxy compound having an epoxy group. Here, in the haloalkyl alcohols represented by X(CH$_2$)$_m$OH, X is a halogen atom such as chlorine, bromine, iodine, or the like, and m is a real number of 2 to 8.

Examples of the compound having the epoxy group encompass glycidol, propylene oxide, glycidyl methyl ether, and isobutylene oxide. Examples of the haloalkyl alcohol encompass 2-chloroethanol, 3-chloropropanol, 4-chlorobutanol, 6-chlorohexanol, 7-chloroheptanol, 8-chlorooctanol, 2-bromoethanol, 3-bromopropanol, 4-bromobutanol, 5-bromopentanol, 6-bromohexanol, 7-bromoheptanol, 8-bromooctanol, 2-iodoethanol, 3-iodopropanol, 4-iodobutanol, 5-iodopentanol, 6-iodohexanol, 7-iodoheptanol, and 8-iodooctanol.

Examples of the phenoxy compound having the epoxy group encompass compounds respectively represented by the following formulae (c-1), (c-2), and (c-3):

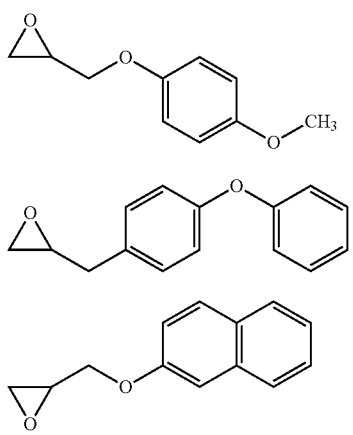

(c-1)

(c-2)

(c-3)

For example, in a case where HOCH$_2$CF$_2$CF$_2$O(CF$_2$CF$_2$CF$_2$O)$_d$CF$_2$CF$_2$CH$_2$OH is used as the compound (b) and glycidol is used as the compound (c), a reaction of these two compounds leads to generation of HOCH$_2$CH(OH)CH$_2$OCH$_2$CF$_2$CF$_2$O(CF$_2$CF$_2$CF$_2$O)$_d$CF$_2$CF$_2$CH$_2$OH as the compound (a).

Meanwhile, for example, in a case where HOCH$_2$CF$_2$CF$_2$O(CF$_2$CF$_2$CF$_2$O)$_d$CF$_2$CF$_2$CH$_2$OH is used as the compound (b) and the compound (c-1) is used as the compound (c), a reaction of these two compounds leads to generation of CH$_3$OC$_6$H$_4$OCH$_2$CH(OH)CH$_2$OCH$_2$CF$_2$CF$_2$O(CF$_2$CF$_2$CF$_2$O)$_d$CF$_2$CF$_2$CH$_2$OH as the compound (a).

<2-2. Synthesis of alkyl compound (A-1) having epoxy group>

The alkyl compound (A-1) having the epoxy group can be obtained by partially epoxidizing the hydroxyl group in a molecule such as the compound (A-2) indicated below.

Examples of the compound (A-2) encompass 2-ethyl-2-(hydroxymethyl)-1,3-propanediol, 2-(hydroxymethyl)-1,3-propanediol, 2-(hydroxymethyl)-2-propyl-1,3-propanediol, 2,2-bis(hydroxymethyl)-1,4-butanediol, 2-(hydroxymethyl)-2-(2-propene-1-yl)-1,3-propanediol, 2-(dihydroxymethyl)-2-(3-methyl butyl)-1,3-propanediol, 2-(hydroxymethyl)-2-(phenylmethyl)-1,3-propanediol, 2-(hydroxymethyl)-2-[(4-nitrophenyl)methyl]-1,3-propanediol, 2-[(4-aminophenyl-9-methyl)-2-(hydroxymethyl)-1,3-propanedi ol, and 2,2-bis(hydroxymethyl)-1,3-propanediol.

Examples of the compound (A-1) encompass compounds respectively represented by the following formulae (D-1), (D-2), and (D-3):

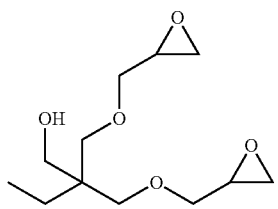

(D-1)

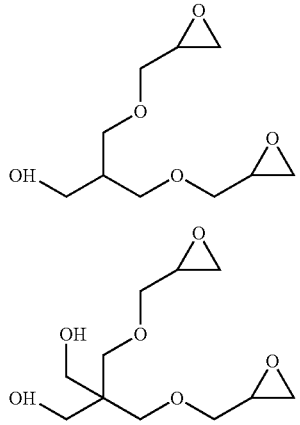

(D-2)

(D-3)

For example, in a case where 2-ethyl-2-(hydroxymethyl)-1,3-propanediol is used as the compound (A-2) and the hydroxyl group thereof is partially epoxidized, 2,2-bis [(2-oxiranylmethoxy)methyl]-1-butanol (compound (D-1)) is generated as the compound (A-1). In a case where 2-(hydroxymethyl)-1,3-propanediol is used as the compound (A-2) and the hydroxyl group thereof is partially epoxidized, 3-(2-oxiranylmethoxy)-2-[(2-oxiranylmethoxy)methyl]-1-propa nol (compound (D-2)) is generated as the compound (A-1). In a case where 2-bis(hydroxymethyl)-1,3-propanediol is used as the compound (A-2) and the hydroxyl group thereof is partially epoxidized, 2,2-bis [(2-oxiranylmethoxy)methyl]-1,3-propanediol (compound (D-3)) is generated as the compound (A-1).

<2-3. Synthesis of perfluoropolyether compound represented by formula (1) as shown in FIG. 3>

The linear fluoropolyether compound (a) having, at the one terminal thereof, the hydroxyl group and having, at the other terminal thereof, the alkoxy group having the hydroxyl group is allowed to react with the alkyl compound (A-1) having the epoxy group in the presence of a base. The reaction temperature is preferably 20° C. to 90° C., more preferably 60° C. to 80° C. The reaction time is preferably 5 hours to 20 hours, more preferably 10 hours to 15 hours. The amount of the compound (A-1) to be used is preferably an equivalent weight of 0.5 to 1.5 with respect to the compound (a). The amount of the base to be used is preferably an equivalent weight of 0.5 to 2.0 with respect to the compound (a). Examples of the base encompass alkaline compounds such as sodium t-butoxide, potassium t-butoxide, sodium hydroxide, potassium hydroxide, and sodium hydride. The reaction may be carried out in a solvent. Examples of the solvent encompass t-butanol, toluene, xylen, and meta-xylene hexafluoride. Thereafter, a product obtained from the reaction is washed with, e.g., water, and then is dehydrated. Consequently, a perfluoropolyether compound represented by the above-indicated formula (1), as shown in FIG. 3, is obtained.

<2-4. Synthesis of Linear Fluoropolyether Compound (d) Having Hydroxyl Group in Perfluoropolyether Chain>

The linear fluoropolyether compound (b) having the hydroxyl groups at both the terminals is allowed to react with epichlorohydrin or epibromohydrin. The reaction temperature is preferably 20° C. to 90° C., more preferably 60° C. to 80° C. The reaction time is preferably 5 hours to 20 hours, more preferably 10 hours to 15 hours. The amount of epichlorohydrin or epibromohydrin to be used is preferably an equivalent weight of 0.2 to 1.5 with respect to the compound (b). The reaction may be carried out with use of a reaction accelerator. Examples of the reaction accelerator encompass sodium hydroxide, potassium t-butoxide, sodium t-butoxide, and sodium hydride. The reaction may be carried out in a solvent. Examples of the solvent encompass t-butyl alcohol, dimethyl formaldehyde, 1,4-dioxane, dimethyl sulfoxide, and dimethylacetamide. Then, a product obtained from the reaction is purified by, e.g., column chromatography. Consequently, a linear fluoropolyether compound (d) having a hydroxyl group in a perfluoropolyether chain is obtained.

<2-5. Synthesis of Perfluoropolyether Compound Represented by Formula (3) as Shown in FIG. 3>

The linear fluoropolyether compound (d) having the hydroxyl group in the perfluoropolyether chain is allowed to react with glycidol in the presence of a base. The reaction temperature is preferably 20° C. to 90° C., more preferably 60° C. to 80° C. The reaction time is preferably 5 hours to 20 hours, more preferably 10 hours to 15 hours. The amount of glycidol to be used is preferably an equivalent weight of 2.0 to 4.0 with respect to the compound (d). The amount of the base to be used is preferably an equivalent weight of 0.2 to 1.0 with respect to the compound (d). Examples of the base encompass alkaline compounds such as sodium t-butoxide, potassium t-butoxide, sodium hydroxide, potassium hydroxide, and sodium hydride. The reaction may be carried out in a solvent. Examples of the solvent encompass t-butanol, toluene, xylen, and meta-xylene hexafluoride. Thereafter, a product obtained from the reaction is washed with, e.g., water, and is then dehydrated. Consequently, a perfluoropolyether compound represented by the above-indicated formula (3), shown in FIG. 3, is obtained.

(3. Lubricant)

A lubricant in accordance with an embodiment of the present invention contains the perfluoropolyether compound in accordance the embodiment of the present invention. The perfluoropolyether compound can be used solely as a lubricant.

Alternatively, the perfluoropolyether compound and other component(s) may be mixed at an arbitrary ratio so as to be used as a lubricant, provided that the performance of the lubricant is not impaired.

Examples of the other component(s) encompass: known lubricants for magnetic disks such as Fomblin (registered trademark), Zdol (available from Solvay Solexis), Ztetraol (available from Solvay Solexis), Demnum (registered trademark) (available from Daikin Industries, Ltd.), and Krytox (registered trademark) (available from Dupont); MORESCO PHOSFAROL A20H (available from MORESCO); and MORESCO PHOSFAROL D-4OH (available from MORESCO).

The lubricant can be used as a lubricant for recording media, in order to improve the sliding properties of magnetic disks. The lubricant can also be used as a lubricant for storage media in other recording devices that involve sliding between a head and a recording medium (e.g., a magnetic tape) other than magnetic disks. The lubricant can be used not only as the lubricant for the recording devices but also as a lubricant for other devices having a part involving sliding.

(4. Magnetic Disk)

As shown in FIG. 1, a magnetic disk 1 in accordance with an embodiment of the present invention includes a recording layer 4, a protective film layer (protective layer) 3, and a lubricant layer 2, which are disposed on a non-magnetic substrate 8. The lubricant layer 2 contains the above-described lubricant.

Figure 2:
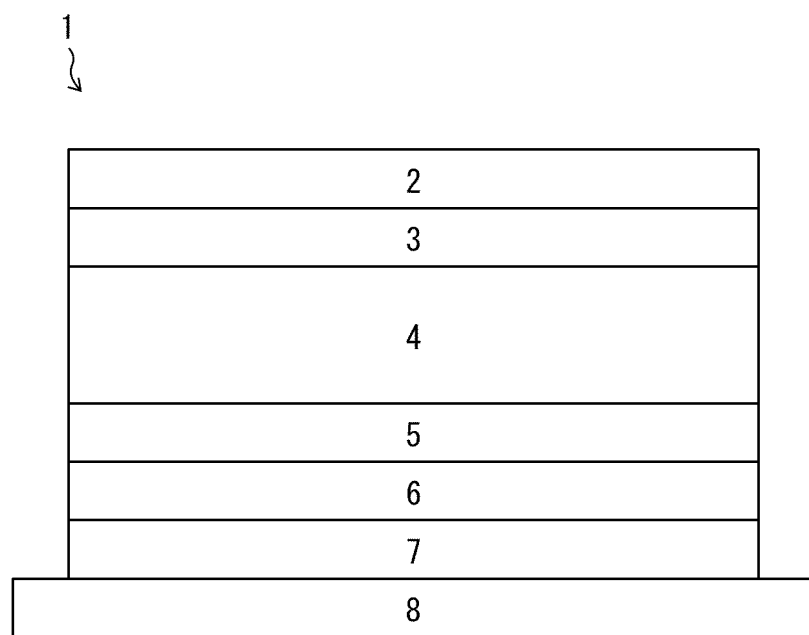
FIG. 2 is a cross-sectional view illustrating a configuration of a magnetic disk in accordance with an embodiment of the present invention.

In another embodiment, a magnetic disk can include, like a magnetic disk 1 illustrated in FIG. 2, a lower layer 5 that underlies the recording layer 4, one or more soft magnetic lower layers 6 that underlie the lower layer 5, and an adhesive layer 7 that underlies the one or more soft magnetic lower layers 6. In one embodiment, all these layers can be formed on the non-magnetic substrate 8.

The layers of the magnetic disk 1 except for the lubricant layer 2 can each contain a material that is known in this technical field to be suitable for a corresponding layer of a magnetic disk. Examples of the material of the recording layer 4 encompass: an alloy of an element (e.g., iron, cobalt, and nickel) from which a ferromagnetic material can be formed and chromium, platinum, tantalum or the like; and an oxide of the alloy. Examples of the material of the protective layer 3 encompass carbon, $Si_3N_4$, SiC, and $SiO_2$. Examples of the material of the non-magnetic substrate 8 encompass an aluminum alloy, glass, and polycarbonate.

(5. Method for Producing Magnetic Disk)

A method in accordance with an aspect of the present invention for producing a magnetic disk includes a step of forming a lubricant layer by placing a lubricant in accordance with an embodiment of the present invention on an exposed surface of a protective layer of a stack of a recording layer and the protective layer.

There is no particular limitation on the method for forming the lubricant layer by placing the lubricant on the exposed surface of the protective layer of the stack of the recording layer and the protective layer. In order to place the lubricant on the exposed surface of the protective layer, it is preferable to dilute the lubricant with a solvent and then to place, on the exposed surface, the lubricant thus diluted. Examples of the solvent encompass: PF-5060, PF-5080, HFE-7100, and HFE-7200 each available from 3M; and Vertrel-XF (registered trademark) available from DuPont. The lubricant diluted with the solvent has a concentration of preferably 0.001 wt % to 1 wt %, more preferably 0.005 wt % to wt %, even more preferably 0.005 wt % to 0.1 wt %. Diluting the lubricant with the solvent so as to have a concentration of 0.005 wt % to 0.1 wt % can weaken the interaction between molecules of the lubricant, which facilitates formation of a uniform lubricant layer.

Alternatively, the recording layer and the protective layer may be formed in this order, the lubricant may be placed on the exposed surface of the protective layer, and then ultraviolet irradiation or heat treatment may be carried out.

The ultraviolet irradiation or heat treatment can form stronger bonds between the lubricant layer and the exposed surface of the protective layer and, in turn, prevent evaporation of the lubricant due to heat. Ultraviolet irradiation is preferably carried out with use of an ultraviolet ray having a wavelength of 185 nm or 254 nm as a dominant wavelength, in order to activate the exposed surface without affecting deep areas of the lubricant layer and the protective layer. The heat treatment is carried out at a temperature of preferably 60° C. to 170° C., more preferably 80° C. to 170° C., even more preferably 80° C. to 150° C.

EXAMPLES

The following description will more specifically discuss the present invention based on Examples. However, the present invention is not limited to the following Examples.

(Evaluation of Bonding Ratio)

In the following Examples, bonding ratios were evaluated in the following manner.

Each of the later-described compounds (0.1 g) was dissolved in Vertrel-XF (550 g) available from DuPont. Subsequently, a magnetic disk of 2.5 inches in diameter was immersed in the obtained solution for three minutes, and then was pulled out at a speed of 2 mm/s. Then, an average film thickness of the compound on the magnetic disk was measured by Fourier Transform Infrared Spectrometer (FT-IR). The film thickness thus obtained was denoted as fÅ. Further, the magnetic disk was immersed in Vertrel-XF for five minutes, and then was pulled out at a speed of 2 mm/s. Thereafter, the magnetic disk was allowed to stand at room temperature so that the solvent was evaporated. Then, an average film thickness of the compound left on the magnetic disk was measured by FT-IR. The film thickness was denoted as bÅ. A bonding ratio was calculated according to the following equation:

Bonding ratio (%)=100×b/f.

The bonding ratio is generally used as an index for indicating the strength of adherence with respect to a magnetic disk.

Example 1

A compound 1 represented by the following formula was synthesized as below.

HOCH$_2$CH(OH)CH$_2$OCH$_2$CF$_2$CF$_2$O(CF$_2$CF$_2$CF$_2$O)$_d$CF$_2$CF$_2$C H$_2$—OCH$_2$CH(OH)CH$_2$OCH$_2$C(CH$_2$CH$_3$)(CH$_2$OH)CH$_2$OCH$_2$CH(OH)C H$_2$O—CH$_2$CF$_2$CF$_2$O (CF$_2$CF$_2$CF$_2$O)$_d$CF$_2$CF$_2$CH$_2$OCH$_2$CH(OH)CH$_2$O H

Figure 4:
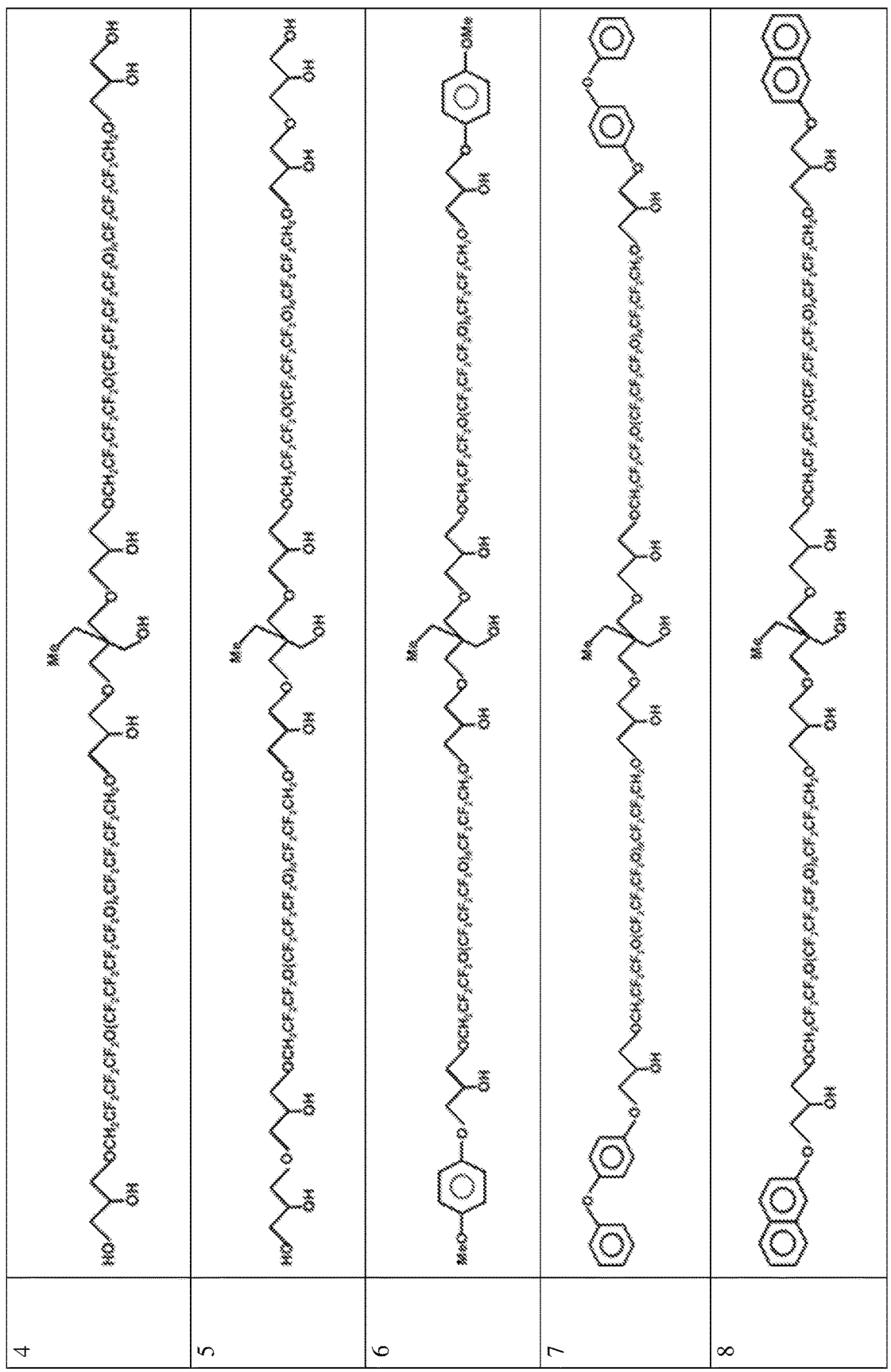
FIG. 4 is a table containing structural formulas for compounds 1-24.
Figure 4:
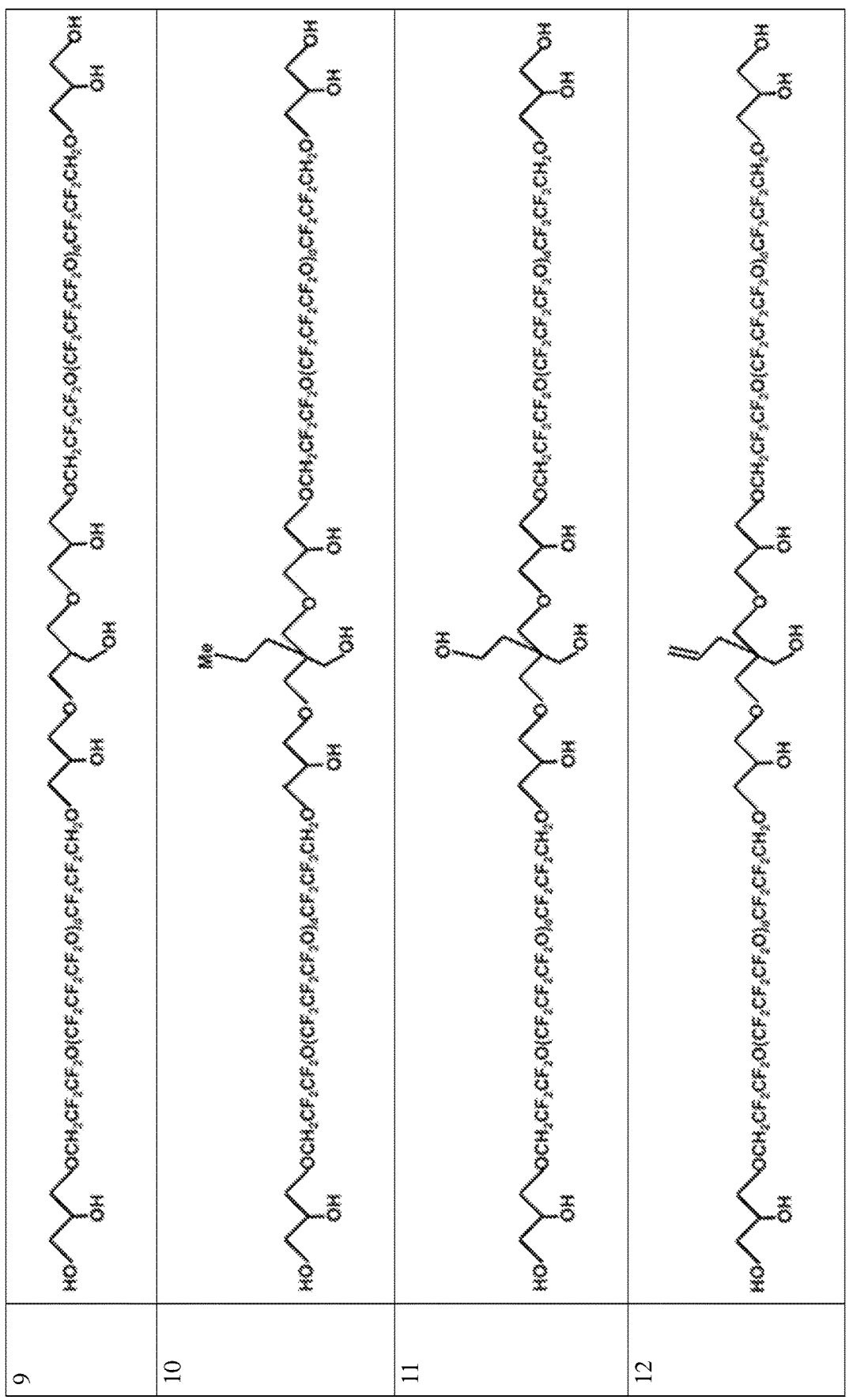
Figure 4:
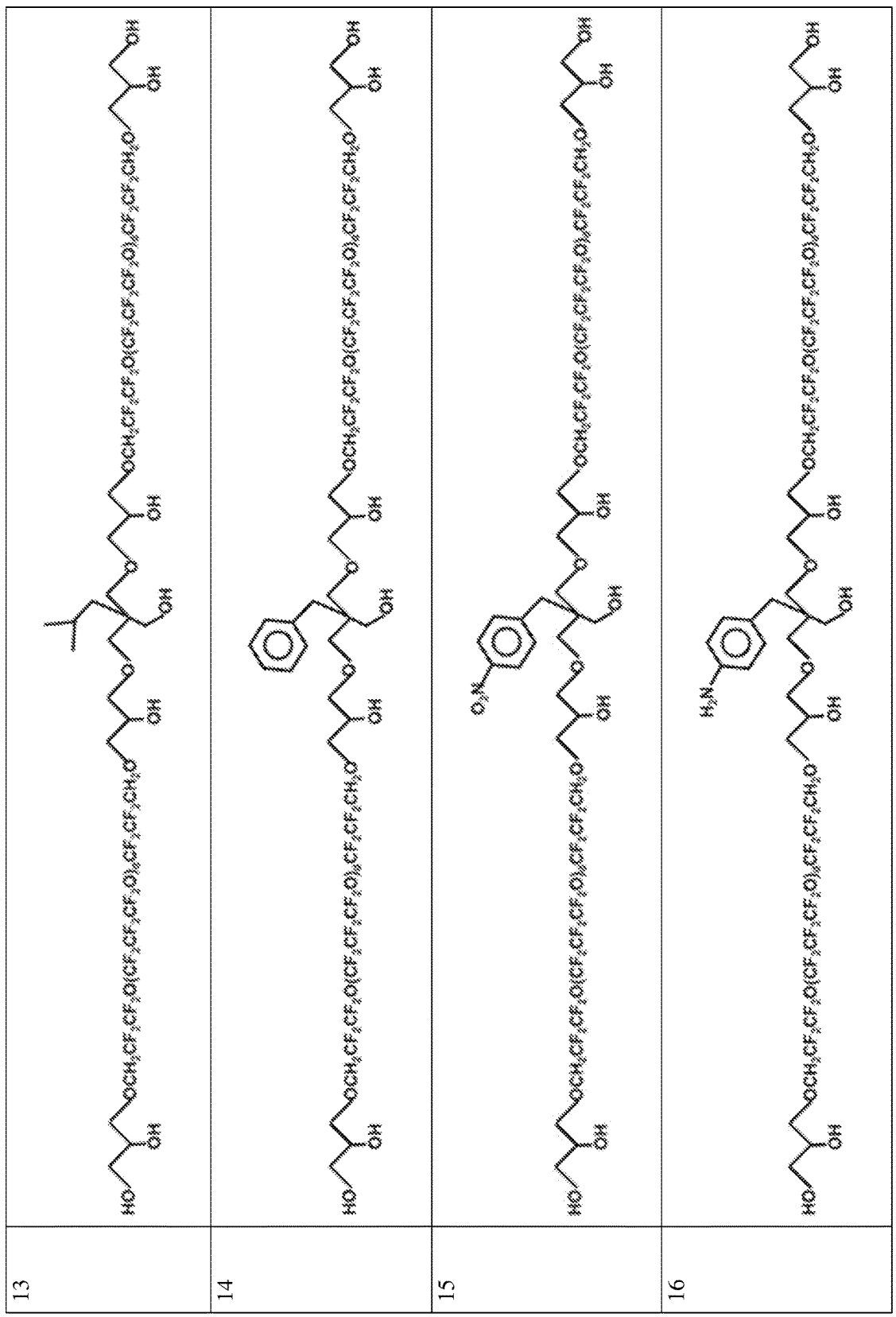

That is, the compound 1 is represented by the structural formula shown in FIG. 4.

The compound 1 corresponds to a compound represented by formula (1), as shown in FIG. 3, where R$^1$ is —CH$_2$CH$_3$, R$^2$ and R$^3$ are each —CH$_2$OCH$_2$CH(OH)CH$_2$OH, and Rf is a perfluoroether having Demnum skeleton.

In an argon atmosphere, 39 g of t-butyl alcohol, 92 g of a fluoropolyether represented by HOCH$_2$CF$_2$CF$_2$O(CF$_2$CF$_2$CF$_2$O)$_d$CF$_2$CF$_2$CH$_2$OH (number average molecular weight: 1141, molecular weight distribution: 1.24), g of potassium t-butoxide, and 5.1 g of glycidol were stirred at 70° C. for 14 hours. Then, a resultant mixture was washed with water, dehydrated, and then purified by silica gel column chromatography. Consequently, 36 g of a perfluoropolyether (average molecular weight: 1152) having one hydroxyl group at one terminal thereof and having two hydroxyl groups at the other terminal thereof was obtained. 36 g of the compound thus obtained was dissolved in 15 g of t-butyl alcohol. 0.3 g of sodium t-butoxide and 2.1 g of a compound obtained by epoxidizing 2-ethyl-2-(hydroxymethyl)-1,3-propanediol were added thereto, and the resultant was stirred at 70° C. for 14 hours. Then, the resultant was washed with water, dehydrated, and then purified by, e.g., distillation. Consequently, 30 g of the compound 1 was obtained.

The compound 1 was a transparent, pale yellow liquid having a density of 1.73 g/cm$^3$ at 20° C. Identification results of the compound 1 by NMR are shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]

δ=−83.7 ppm [20F, —OCF$_2$CF$_2$CF$_2$O—]

δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

The results of $^{19}$F-NMR demonstrate that the compound 1 had d=5.2.

$^1$H-NMR (solvent: none, reference material: D$_2$O)

δ=2.5 ppm to 5.0 ppm [41H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH) CH$_2$OCH$_2$CH(OH)CH$_2$O—CH$_2$CF$_2$CF$_2$O(CF$_2$CF$_2$CF$_2$O)$_d$ CF$_2$CF$_2$CH$_2$OCH$_2$CH(OH)CH$_2$OH]

δ=1.3 ppm [2H, HOCH$_2$CH(OH)CH$_2$OCH$_2$CF$_2$CF$_2$O (CF$_2$CF$_2$CF$_2$O)$_d$CF$_2$CF$_2$CF$_{12}$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=0.9 ppm [3H, HOCH$_2$CH(OH)CH$_2$OCH$_2$CF$_2$CF$_2$O (CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

The compound 1 thus obtained was used as a lubricant of Example 1.

Example 2

A compound 2 represented by the following formula was synthesized as below.

HOCH$_2$CH(OH)CH$_2$OCH$_2$CF$_2$O(CF$_2$O)$_b$(CF$_2$CF$_2$O)$_c$CF$_2$CH$_2$—OCH$_2$CH(OH)CH$_2$OCH$_2$C(CH$_2$CH$_3$)(CH$_2$OH) CH$_2$OCH$_2$CH(OH)CH$_2$—CHCF$_2$O(CF$_2$O)$_b$ (CF$_2$CF$_2$O)$_c$ CF$_2$CH$_2$O CH$_2$CH(OH)CH$_2$OH

That is, the compound 2 is represented by the structural formula shown in FIG. 4.

20 g of the compound 2 was obtained in the same manner as in Example 1, except that the fluoropolyether represented by HOCH$_2$CF$_2$CF$_2$O(CF$_2$CF$_2$CF$_2$O)$_d$CF$_2$CF$_2$CH$_2$OH was replaced by a fluoropolyether represented by HOCH$_2$CF$_2$O (CF$_2$O)$_b$ (CF$_2$CF$_2$O)$_c$CF$_2$CH$_2$OH.

The compound 2 was a transparent, pale yellow liquid having a density of 1.72 g/cm$^3$ at 20° C. Identification results of the compound 2 are as shown below.

$^{19}$F-NMR (solvent: none, reference material: OCF$_2$CF$_2$CF$_2$O in the product [−125.8 ppm])=

δ=−52.1 ppm, −53.7 ppm, −55.4 ppm [10F, —OCF$_2$O—]

δ=−89.1 ppm, −90.7 ppm [20F, —OCF$_2$CF$_2$O—]

δ=−77.9 ppm, −80.0 ppm [8F, —OCF$_2$CH$_2$OCH$_2$CH(OH)CH$_2$O—, —OCF$_2$CH$_2$OCH$_2$CH(OH)CH$_2$OH]

The results of $^{19}$F-NMR demonstrate that the compound 2 had b=5.1 and c=5.0.

$^1$H-NMR (solvent: none, reference material: D$_2$O)

δ=2.5 ppm to 5.0 ppm [41H, HOCH$_2$CH(OH) CH$_2$OCH$_2$CF$_2$O(CF$_2$O)$_b$(CF$_2$CF$_2$O)$_c$CF$_2$CH$_2$—OCH$_2$C H(OH)CH$_2$O CH$_2$C(CH$_2$CH$_3$) (CH$_2$OH)CH$_2$OCH$_2$CH (OH) CH$_2$O—CH$_2$C F$_2$O(CF$_2$O)$_b$(CF$_2$CF$_2$O)$_c$ CF$_2$CH$_2$OCH$_2$CH(OH)CH$_2$OH]

δ=1.3 ppm [2H, HOCH$_2$CH(OH)CH$_2$OCH$_2$CF$_2$O(CF$_2$O)$_b$(CF$_2$CF$_2$O)$_c$CF$_2$CH$_2$—OCH$_2$C H(OH)CH$_2$OCH$_2$C (CH$_2$CH$_3$) (CH$_2$OH)CH$_2$OCH$_2$CH(OH) CH$_2$O—CH$_2$C F$_2$O(CF$_2$O)$_b$(CF$_2$CF$_2$O)$_c$CF$_2$CH$_2$OCH$_2$CH(OH)CH$_2$OH]

δ=0.9 ppm [3H, HOCH$_2$CH(OH)CH$_2$OCH$_2$CF$_2$O(CF$_2$O)$_b$(CF$_2$CF$_2$O)$_c$CF$_2$CH$_2$—OCH$_2$C H(OH)CH$_2$OCH$_2$C(CH$_2$CH$_3$)(CH$_2$OH)CH$_2$OCH$_2$CH(OH)CH$_2$O—CH$_2$C F$_2$O (CF$_2$O)$_b$ (CF$_2$CF$_2$O)$_c$CF$_2$CH$_2$OCH$_2$CH(OH)CH$_2$OH]

The compound 2 thus obtained was used as a lubricant of Example 2.

Example 3

A compound 3 represented by the following formula was synthesized as below.

HOCH$_2$CH(OH)CH$_2$OCH$_2$CF$_2$O(CF$_2$CF$_2$O)$_c$CF$_2$CH$_2$—OCH$_2$CH(OH) CH$_2$OCH$_2$C(CH$_2$CH$_3$) (CH$_2$OH)

CH₂OCH₂CH(OH)CH₂O—CH₂CF₂O(CF₂CF₂O)_c CF₂CH₂OCH₂CH(OH)CH₂OH

That is, the compound 3 is represented by the structural formula shown in FIG. 4.

30 g of the compound 3 was obtained in the same manner as in Example 1, except that the fluoropolyether represented by HOCH₂CF₂CF₂O(CF₂CF₂CF₂O)_dCF₂CF₂CH₂OH was replaced by a fluoropolyether represented by HOCH₂CF₂O(CF₂CF₂O)_cCF₂CH₂OH.

The compound 3 was a waxy, white solid having a density of 1.73 g/cm³ at 20° C. Identification results of the compound 3 by NMR are as shown below.

¹⁹F-NMR (solvent: none, reference material: OCF₂CF₂O in the product [89.1 ppm])

δ=−89.1 ppm [32F, —OCF₂CF₂O—]
δ=−79.0 ppm [8F, —OCF₂CH₂OCH₂CH(OH)CH₂O—, CF₂CH₂OCH₂CH(OH)CH₂OH]

The results of ¹⁹F-NMR demonstrate that the compound 3 had c=8.5.

¹H-NMR (solvent: none, reference material: D₂O)
δ=2.5 ppm to 5.0 ppm [41H, HOCH₂CH(OH)CH₂OCH₂CF₂O(CF₂CF₂O)_cCF₂CH₂—OCH₂CH(OH)CH₂OCH₂C(CH₂CH₃)(CH₂OH)CH₂OCH₂CH(OH)CH₂O—CH₂CF₂O(CF₂CF₂O)_cCF₂CH₂OCH₂CH(OH)CH₂OH]
δ=1.3 ppm [2H, HOCH₂CH(OH)CH₂OCH₂CF₂O(CF₂CF₂O)_cCF₂CH₂—OCH₂CH(OH)C H₂OCH₂C(CH₂CH₃)(CH₂OH)CH₂OCH₂CH(OH)CH₂O—CH₂CF₂O(CF₂CF₂O)_cCF₂CH₂OCH₂CH(OH)CH₂OH]
δ=0.9 ppm [3H, HOCH₂CH(OH)CH₂OCH₂CF₂O(CF₂CF₂O)_cCF₂CH₂—OCH₂CH(OH)C H₂OCH₂C(CH₂CH₃)(CH₂OH)CH₂OCH₂CH(OH)CH₂O—CH₂CF₂O(CF₂CF₂O)_cCF₂CH₂OCH₂CH(OH)CH₂OH]

The compound 3 thus obtained was used as a lubricant of Example 3.

Example 4

A compound 4 represented by the following formula was synthesized as below.

HOCH₂CH(OH)CH₂OCH₂CF₂CF₂CF₂O(CF₂CF₂CF₂CF₂O)_eC F₂CF₂CF₂CH₂—OCH₂CH(OH)CH₂OCH₂C(CH₂CH₃)(CH₂OH)CH₂OC H₂CH(OH)CH₂O—CH₂CF₂CF₂CF₂O(CF₂CF₂CF₂CF₂O)_eCF₂CF₂CF₂C H₂OCH₂CH(OH)CH₂OH

That is, the compound 4 is represented by the structural formula shown in FIG. 4.

33 g of the compound 4 was obtained in the same manner as in Example 1, except that the fluoropolyether represented by HOCH₂CF₂CF₂O(CF₂CF₂CF₂O)_dCF₂CF₂CH₂OH was replaced by a fluoropolyether represented by HOCH₂CF₂CF₂CF₂O(CF₂CF₂CF₂CF₂O)_eCF₂CF₂CF₂CH₂OH.

The compound 4 was a colorless, transparent liquid having a density of 1.72 g/cm³ at 20° C. Identification results of the compound 4 by NMR are as shown below.

¹⁹F-NMR (solvent: none, reference material: OCF₂CF₂CF₂CF₂O in the product [−125.8 ppm])

δ=−83.7 ppm [20F, —OCF₂CF₂CF₂O—, —OCF₂CF₂CF₂CH₂OCH₂CH(OH)CH₂O—, —OCF₂CF₂CF₂CH₂OCH₂CH(OH)CH₂OH]
δ=−123.3 pm [8F, —OCF₂CF₂CF₂CH₂OCH₂CH(OH)CH₂O—, —OCF₂CF₂CF₂CH₂OCH₂CH(OH)CH₂OH]
δ=−125.8 ppm [12F, —OCF₂CF₂CF₂CF₂O—]
δ=−127.6 ppm [8F, —OCF₂CF₂CF₂CH₂OCH₂CH(OH)CH₂O—, —OCF₂CF₂CF₂CH₂OCH₂CH(OH)CH₂OH]

The results of ¹⁹F-NMR demonstrate that the compound 4 had e=3.2.

¹H-NMR (solvent: none, reference material: D₂O)
δ=2.5 to 5.0 ppm [41H, HOCH₂CH(OH)CH₂OCH₂CF₂CF₂CF₂O(CF₂CF₂CF₂CF₂O)_e CF₂CF₂CF₂CH₂—OCH₂CH(OH)CH₂OCH₂C(CH₂CH₃)(CH₂OH)CH₂OCH₂CH(OH)CH₂O—CH₂CF₂CF₂CF₂O(CF₂CF₂O)_eCF₂CF₂CF₂CH₂OCH₂CH(OH)CH₂OH]
δ=1.3 ppm [2H, HOCH₂CH(OH)CH₂OCH₂CF₂CF₂CF₂O(CF₂CF₂CF₂CF₂O)_e CF₂CF₂CF₂CH₂—OCH₂CH(OH)CH₂OCH₂C(CH₂CH₃)(CH₂OH)CH₂OCH₂CH(OH)CH₂O—CH₂CF₂CF₂CF₂O(CF₂CF₂CF₂CF₂O)_eCF₂CF₂CF₂CH₂OC H₂CH(OH)CH₂OH]
δ=0.9 ppm [3H, HOCH₂CH(OH)CH₂OCH₂CF₂CF₂CF₂O(CF₂CF₂CF₂CF₂O)_e CF₂CF₂CF₂CH₂—OCH₂CH(OH)CH₂OCH₂C(CH₂CH₃)(CH₂OH)CH₂OCH₂CH(OH)CH₂O—CH₂CF₂CF₂CF₂O (CF₂CF₂O)_eCF₂CF₂CF₂CH₂OCH₂CH(OH)CH₂OH]

The compound 4 thus obtained was used as a lubricant of Example 4.

Example 5

A compound 5 represented by the following formula was synthesized as below.

HOCH₂CH(OH)CH₂OCH₂CH(OH)CH₂OCH₂CF₂CF₂O(CF₂CF₂CF₂O)_dCF₂CF₂CH₂—OCH₂CH(OH)CH₂OCH₂C(CH₂CH₃)(CH₂OH)C H₂OCH₂CH(OH)CH₂O—CH₂CF₂CF₂O(CF₂CF₂CF₂O)_dCF₂CF₂CH₂O CH₂CH(OH)CH₂OCH₂CH(OH)CH₂OH

That is, the compound 5 is represented by the structural formula shown in FIG. 4.

In an argon atmosphere, 39 g of t-butyl alcohol, 90 g of fluoropolyether (number average molecular weight: 1050, molecular weight distribution: 1.50) represented by HO—CH₂CF₂CF₂O(CF₂CF₂CF₂O)_dCF₂CF₂CH₂—OH, 0.9 g of potassium t-butoxide, and 11.0 g of glycidol were stirred at 70° C. for 14 hours. Then, a resultant mixture was washed with water, dehydrated, and then purified by silica gel column chromatography. Consequently, 83 g of a perfluoropolyether (average molecular weight: 1100) having one hydroxyl group at one terminal thereof and having two hydroxyl groups at the other terminal thereof was obtained. 83 g of the compound thus obtained was dissolved in 36 g of t-butyl alcohol. Then, 0.6 g of sodium t-butoxide and 5.1 g of 2,2-bis[(2-oxiranylmethoxy)methyl]-1-butanol were added thereto, and the resultant was stirred at 70° C. for 14 hours. Then, the resultant was washed with water, dehydrated, and then purified by distillation or the like. Consequently, 58 g of the compound 5 was obtained.

The compound 5 was a transparent, pale yellow liquid having a density of 1.75 g/cm³ at 20° C. Identification results of the compound 5 by NMR are as shown below.

¹⁹F-NMR (solvent: none, reference material: OCF₂CF₂O in the product [−129.7 ppm])

δ=−129.7 ppm [10F, —OCF₂CF₂CF₂O—]
δ=−83.7 ppm [20F, —OCF₂CF₂CF₂O—]
δ=−124.2 ppm [8F, —OCF₂CF₂CH₂OCH₂CH(OH)CH₂O—, —OCF₂CF₂CH₂OCH₂CH(OH)CH₂OCH₂CH(OH)CH₂OH]
δ=−86.5 ppm [8F, —OCF₂CF₂CH₂OCH₂CH(OH)CH₂O—, —OCF₂CF₂CH₂OCH₂CH(OH)CH₂OCH₂CH(OH)CH₂OH]

The results of ¹⁹F-NMR demonstrate that the compound 5 had d=5.0.

¹H-NMR (solvent: none, reference material: D₂O) δ=2.5 ppm to 5.0 ppm [53H, HOCH₂CH(OH)CH₂OCH₂CH(OH)CH₂OCH₂CF₂CF₂O(CF₂CF₂CF₂O)_dCF₂CF₂CH₂—OCH₂CH(OH)CH₂OCH₂C(CH₂CH₃)(CH₂OH)CH₂OC H₂CH(OH)CH₂O—CH₂CF₂CF₂O(CF₂CF₂CF₂O)_d CF₂CF₂CH₂OCH₂C H(OH)CH₂OCH₂CH(OH)CH₂OH]
δ=1.3 ppm [2H, HOCH₂CH(OH)CH₂OCH₂CH(OH)CH₂OCH₂CF₂CF₂O(CF₂CF₂CF₂O)_dCF₂CF₂CH₂—

OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$C H(OH)CH$_2$OCH$_2$CH(OH)CH$_2$OH]

δ=0.9 ppm [3H, HOCH$_2$CH(OH)CH$_2$OCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$C H(OH)CH$_2$OCH$_2$CH(OH)CH$_2$OH]

The compound 5 thus obtained was used as a lubricant of Example 5.

Example 6

A compound 6 represented by the following formula was synthesized as below.
CH$_3$OC$_6$H$_4$OCH$_2$CH(OH)CH$_2$OCH$_2$CF$_2$CF$_2$O(CF$_2$CF$_2$CF$_2$O)$_d$ CF$_2$CF$_2$CH$_2$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OC$_6$H$_4$OCH$_3$ That is, the compound 6 is represented by the structural formula shown in FIG. 4.

40 g of the compound 6 was obtained in the same manner as in Example 1, except that glycidol was replaced by the compound (c-1).

The compound 6 was a transparent, pale yellow liquid having a density of 1.76 g/cm$^3$ at 20° C. Identification results of the compound 6 by NMR are as shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]
δ=−83.7 ppm [20F, —OCF$_2$CF$_2$CF$_2$O—]
δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OC$_6$H$_4$OCH$_3$]
δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OC$_6$H$_4$OCH$_3$]

The results of $^{19}$F-NMR demonstrate that the compound 6 had d=5.2.

$^1$H-NMR (solvent: none, reference material: D$_2$O)

δ=2.5 to 5.0 ppm [45H, CH$_3$OC$_6$H$_4$OCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH)CH$_2$OCH$_2$CH(O H)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OC$_6$H$_4$OCH$_3$]
δ=1.3 ppm [2H, CH$_3$OC$_6$H$_4$OCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH)CH$_2$OCH$_2$CH(O H)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OC$_6$H$_4$OCH$_3$]
δ=0.9 ppm [3H, CH$_3$OC$_6$H$_4$OCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH)CH$_2$OCH$_2$CH(O H)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OC$_6$H$_4$OCH$_3$]
δ=6.5 ppm to 7.5 ppm [8H, —OCF$_2$CF$_2$CH$_2$OCH$_2$CH(OH) CH$_2$OC$_6$H$_4$OCH$_3$]

The compound 6 thus obtained was used as a lubricant of Example 6.

Example 7

A compound 7 represented by the following formula was synthesized as below.
C$_6$H$_5$OC$_6$H$_4$OCH$_2$CH(OH)CH$_2$OCH$_2$CF$_2$CF$_2$O(CF$_2$CF$_2$CF$_2$O)$_d$ CF$_2$CF$_2$CH$_2$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(O H)CH$_2$OC$_6$H$_4$OC$_6$H$_5$ That is, the compound 7 is represented by the structural formula shown in FIG. 4.

46 g of the compound 7 was obtained in the same manner as in Example 1, except that glycidol was replaced by the compound (c-2).

The compound 7 was a colorless, transparent liquid having a density of 1.76 g/cm$^3$ at 20° C. Identification results of the compound 7 by NMR are as shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]
δ=−83.7 ppm [20F, —OCF$_2$CF$_2$CF$_2$O—]
δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OC$_6$H$_4$OC$_6$H$_5$]
δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OC$_6$H$_4$OC$_6$H$_5$]

The results of $^{19}$F-NMR demonstrate that the compound 7 had d=5.2.

$^1$H-NMR (solvent: none, reference material: D$_2$O)

δ=2.5 ppm to 5.0 ppm [39H, C$_6$H$_5$OC$_6$H$_4$OCH$_2$CH(OH)CH$_2$OCH$_2$CF$_2$CF$_2$O(CF$_2$CF$_2$CF$_2$O)$_d$CF$_2$C F$_2$CH$_2$—OCH$_2$CH(OH)CH$_2$OCH$_2$C(CH$_2$CH$_3$) (CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OC$_6$H$_4$OC$_6$H$_5$]
δ=1.3 ppm [2H, C$_6$H$_5$OC$_6$H$_4$OCH$_2$CH(OH)CH$_2$OCH$_2$CF$_2$CF$_2$O(CF$_2$CF$_2$CF$_2$O)$_d$CF$_2$C F$_2$CH$_2$—OCH$_2$CH(OH)CH$_2$OCH$_2$C(CH$_2$CH$_3$)(CH$_2$OH) CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OC$_6$H$_4$OC$_6$H$_5$]
δ=0.9 ppm [3H, C$_6$H$_5$OC$_6$H$_4$OCH$_2$CH(OH)CH$_2$OCH$_2$CF$_2$CF$_2$O(CF$_2$CF$_2$CF$_2$O)$_d$CF$_2$C F$_2$CH$_2$—OCH$_2$CH(OH)CH$_2$OCH$_2$C(CH$_2$CH$_3$) (CH$_2$OH) CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OC$_6$H$_4$OC$_6$H$_5$]
δ=6.5 ppm to 7.5 ppm [18H, —OCF$_2$CF$_2$CH$_2$OCH$_2$CH(OH)CH$_2$OC$_6$H$_4$OC$_6$H$_5$]

The compound 7 thus obtained was used as a lubricant of Example 7.

Example 8

A compound 8 represented by the following formula was synthesized as below.
C$_{10}$H$_7$OCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OC$_{10}$H$_7$ That is, the compound 8 is represented by the structural formula shown in FIG. 4.

19 g of the compound 8 was obtained in the same manner as in Example 1, except that glycidol was replaced by the compound (c-3).

The compound 8 was a colorless, transparent liquid having a density of 1.76 g/cm$^3$ at 20° C. Identification results of the compound 8 by NMR are as shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]
δ=−83.7 ppm [20F, —OCF$_2$CF$_2$CF$_2$O—]
δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OC$_{10}$H$_7$]
δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OC$_{10}$H$_7$]

The results of $^{19}$F-NMR demonstrate that the compound 8 had d=5.1.

$^1$H-NMR (solvent: none, reference material: $D_2O$)

δ=2.5 ppm to 5.0 ppm [39H, $C_{10}H_7OCH_2CH(OH)$ $CH_2OCH_2CF_2CF_2O(CF_2CF_2CF_2O)_dCF_2CF_2CH_2$—$OCH_2CH(OH)CH_2OCH_2C(CH_2CH_3)$ $(CH_2OH)$ $CH_2OCH_2CH(OH)CH_2O$—$CH_2CF_2CF_2O(CF_2CF_2CF_2O)_d$ $CF_2CF_2CH_2OCH_2CH(OH)CH_2OC_{10}H_7$]

δ=1.3 ppm [2H, $C_{10}H_7OCH_2CH(OH)$ $CH_2OCH_2CF_2CF_2O(CF_2CF_2CF_2O)_dCF_2CF_2CH_2$—$OCH_2CH(OH)$ $CH_2OCH_2C(CH_2CH_3)$ $(CH_2OH)$ $CH_2OCH_2CH(OH)CH_2O$—$CH_2CF_2CF_2O(CF_2CF_2CF_2O)_d$ $CF_2CF_2CH_2OCH_2CH(OH)CH_2OC_{10}H_7$]

δ=0.9 ppm [3H, $C_{10}H_7OCH_2CH(OH)$ $CH_2OCH_2CF_2CF_2O(CF_2CF_2CF_2O)_dOCF_2OCF_2OCH_2$—$OCH_2CH(OH)CH_2OCH_2C(CH_2CH_3)(CH_2OH)$ $CH_2OCH_2CH(OH)CH_2O$—$CH_2CF_2CF_2O(CF_2CF_2CF_2O)_d$ $CF_2CF_2CH_2OCH_2CH(OH)CH_2OC_{10}H_7$]

δ=6.5 ppm to 7.5 ppm [14H, —$OCF_2CF_2CH_2OCH_2CH(OH)CH_2OC_{10}H_7$]

The compound 8 thus obtained was used as a lubricant of Example 8.

Example 9

A compound 9 represented by the following formula was synthesized as below.

$HOCH_2CH(OH)CH_2OCH_2CF_2CF_2O(CF_2CF_2CF_2O)_d$ $CF_2CF_2C$ $H_2$—$OCH_2CH(OH)CH_2OCH_2CH(CH_2OH)$ $CH_2OCH_2CH(OH)CH_2O$—$CH_2CF_2CF_2O(CF_2CF_2CF_2O)_d$ $CF_2CF_2CH_2OCH_2CH(OH)CH_2OH$

That is, the compound 9 is represented by the structural formula shown in FIG. 4.

51 g of the compound 9 was obtained in the same manner as in Example 1, except that 2-ethyl-2-(hydroxymethyl)-1, 3-propanediol was replaced by 2-(hydroxymethyl)-1,3-propanediol.

The compound 9 was a transparent, pale yellow liquid having a density of 1.74 g/cm³ at 20° C. Identification results of the compound 9 by NMR are as shown below.

$^{19}$F-NMR (solvent: none, reference material: $OCF_2CF_2CF_2O$ in the product [−129.7 ppm])

δ=−129.7 ppm [10F, —$OCF_2CF_2CF_2O$—]

δ=−83.7 ppm [20F, —$OCF_2CF_2CF_2O$—]

δ=−124.2 ppm [8F, —$OCF_2CF_2CH_2OCH_2CH(OH)CH_2O$—, —$OCF_2CF_2CH_2OCH_2CH(OH)CH_2OH$]

δ=−86.5 ppm [8F, —$OCF_2CF_2CH_2OCH_2CH(OH)CH_2O$—, —$OCF_2CF_2CH_2OCH_2CH(OH)CH_2OH$]

The results of $^{19}$F-NMR demonstrate that the compound 9 had d=5.3.

$^1$H-NMR (solvent: none, reference material: $D_2O$)

δ=2.5 ppm to 5.0 ppm [41H, $HOCH_2CH(OH)$ $CH_2OCH_2CF_2CF_2O(CF_2CF_2CF_2O)_dCF_2CF_2CH_2$—$OCH_2CH(OH)CH_2OCH_2CH(CH_2OH)$ $CH_2OCH_2CH(OH)CH_2O$—$CH_2CF_2C$ $F_2O(CF_2CF_2CF_2O)_d$ $CF_2CF_2CH_2OCH_2CH(OH)CH_2OH$]

δ=2.2 ppm [1H, $HOCH_2CH(OH)CH_2OCH_2CF_2CF_2O$ $(CF_2CF_2CF_2O)_dCF_2CF_2CH_2$—$OC$ $H_2CH(OH)$ $CH_2OCH_2CH(CH_2OH)CH_2OCH_2CH(OH)CH_2O$—$CH_2CF_2C$ $F_2O(CF_2CF_2CF_2O)_aCF_2CF_2CH_2OCH_2CH(OH)$ $CH_2OH$]

The compound 9 thus obtained was used as a lubricant of Example 9.

Example 10

A compound 10 represented by the following formula was synthesized as below.

$HOCH_2CH(OH)CH_2OCH_2CF_2CF_2O(CF_2CF_2CF_2O)_d$ $CF_2CF_2C$ $H_2$—$OCH_2CH(OH)CH_2OCH_2C(CH_2CH_2CH_3)$ $(CH_2OH)CH_2OCH_2CH(OH)CH_2O$—$CH_2CF_2CF_2O$ $(CF_2CF_2CF_2O)_dCF_2CF_2CH_2OCH_2CH(OH)C$ $H_2OH$

That is, the compound 10 is represented by the structural formula shown in FIG. 4.

24 g of the compound 10 was obtained in the same manner as in Example 1, except that 2-ethyl-2-(hydroxymethyl)-1,3-propanediol was replaced by 2-(hydroxymethyl)-2-propyl-1,3-propanediol.

The compound 10 was a transparent, pale yellow liquid having a density of 1.73 g/cm³ at 20° C. Identification results of the compound 10 by NMR are as shown below.

$^{19}$F-NMR (solvent: none, reference material: $OCF_2CF_2CF_2O$ in the product [−129.7 ppm])

δ=−129.7 ppm [10F, —$OCF_2CF_2CF_2O$—]

δ=−83.7 ppm [20F, —$OCF_2CF_2CF_2O$—]

δ=−124.2 ppm [8F, —$OCF_2CF_2CH_2OCH_2CH(OH)CH_2O$—, —$OCF_2CF_2CH_2OCH_2CH(OH)CH_2OH$]

δ=−86.5 ppm [8F, —$OCF_2CF_2CH_2OCH_2CH(OH)CH_2O$—, —$OCF_2CF_2CH_2OCH_2CH(OH)CH_2OH$]

The results of $^{19}$F-NMR demonstrate that the compound 10 had d=5.0.

$^1$H-NMR (solvent: none, reference material: $D_2O$)

δ=2.5 ppm to 5.0 ppm [41H, $HOCH_2CH(OH)$ $CH_2OCH_2CF_2CF_2O(CF_2CF_2CF_2O)_dCF_2CF_2CH_2$—$OCH_2CH(OH)CH_2OCH_2C(CH_2CH_2CH_3)(CH_2OH)$ $CH_2OCH_2CH(OH)CH_2O$—$CH_2CF_2CF_2O(CF_2CF_2CF_2O)_d$ $CF_2CF_2CH_2OCH_2CH(OH)CH_2OH$]

δ=0.5 ppm to 1.5 ppm [7H, $HOCH_2CH(OH)$ $CH_2OCH_2CF_2CF_2O(CF_2CF_2CF_2O)_dCF_2CF_2CH_2$—$OCH_2CH(OH)CH_2OCH_2C(CH_2CH_2CH_3)(CH_2OH)$ $CH_2OCH_2CH(OH)CH_2O$—$CH_2CF_2CF_2O(CF_2CF_2CF_2O)_d$ $CF_2CF_2CH_2OCH_2CH(OH)CH_2OH$]

The compound 10 thus obtained was used as a lubricant of Example 10.

Example 11

A compound 11 represented by the following formula was synthesized as below.

$HOCH_2CH(OH)CH_2OCH_2CF_2CF_2O(CF_2CF_2CF_2O)_d$ $CF_2CF_2C$ $H_2$—$OCH_2CH(OH)CH_2OCH_2C(CH_2CH_2OH)$ $(CH_2OH)CH_2OCH_2CH(OH)CH_2O$—$CH_2CF_2CF_2O$ $(CF_2CF_2CF_2O)_dCF_2CF_2CH_2OCH_2CH(OH)CH_2OH$

That is, the compound 11 is represented by the structural formula shown in FIG. 4.

25 g of the compound 11 was obtained in the same manner as in Example 1, except that 2-ethyl-2-(hydroxymethyl)-1, 3-propanediol was replaced by 2,2-bis(hydroxymethyl)-1,4-butanediol.

The compound 11 was a transparent, pale yellow liquid having a density of 1.73 g/cm³ at 20° C. Identification results of the compound 11 by NMR are as shown below.

$^{19}$F-NMR (solvent: none, reference material: $OCF_2CF_2CF_2O$ in the product [−129.7 ppm])

δ=−129.7 ppm [10F, —$OCF_2CF_2CF_2O$—]

δ=−83.7 ppm [20F, —$OCF_2CF_2CF_2O$—]

δ=−124.2 ppm [8F, —$OCF_2CF_2CH_2OCH_2CH(OH)CH_2O$—, —$OCF_2CF_2CH_2OCH_2CH(OH)CH_2OH$]

δ=−86.5 ppm [8F, —$OCF_2CF_2CH_2OCH_2CH(OH)CH_2O$—, —$OCF_2CF_2CH_2OCH_2CH(OH)CH_2OH$]

The results of $^{19}$F-NMR demonstrate that the compound 11 had d=5.1.

$^1$H-NMR (solvent: none, reference material: $D_2O$)

δ=2.5 ppm to 5.0 ppm [44H, $HOCH_2CH(OH)$ $CH_2OCH_2CF_2CF_2O(CF_2CF_2CF_2O)_dCF_2CF_2CH_2$—$OCH_2CH(OH)CH_2OCH_2C(CH_2CH_2OH)(CH_2OH)$ $CH_2OCH_2CH(OH)CH_2O$—$CH_2CF_2CF_2O(CF_2CF_2CF_2O)_d$ $CF_2CF_2CH_2OCH_2CH(OH)CH_2OH$]

δ=1.8 ppm [2H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_2$OH)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

The compound 11 thus obtained was used as a lubricant of Example 11.

Example 121

A compound 12 represented by the following formula was synthesized as below.
HOCH$_2$CH(OH)CH$_2$OCH$_2$CF$_2$CF$_2$O(CF$_2$CF$_2$CF$_2$O)$_d$CF$_2$CF$_2$C H$_2$—OCH$_2$CH(OH)CH$_2$OCH$_2$C(CH$_2$CHCH$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH That is, the compound 12 is represented by the structural formula shown in FIG. 4.

33 g of the compound 12 was obtained in the same manner as in Example 1, except that 2-ethyl-2-(hydroxymethyl)-1,3-propanediol was replaced by 2-(hydroxymethyl)-2-(2-propane-1-yl)-1,3-propanediol.

The compound 12 was a transparent, pale yellow liquid having a density of 1.74 g/cm$^3$ at 20° C. Identification results of the compound 12 by NMR are as shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]
δ=−83.7 ppm [20F, —OCF$_2$CF$_2$CF$_2$O—]
δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]
δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

The results of $^{19}$F-NMR demonstrate that the compound 12 had d=5.1.

$^1$H-NMR (solvent: none, reference material: D$_2$O)
δ=2.5 ppm to 5.0 ppm [41H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CHCH$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=2.2 ppm [2H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CHCH$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=4.8 ppm and 5.8 ppm [3H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CHCH$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

The compound 12 thus obtained was used as a lubricant of Example 12.

Example 13

A compound 13 represented by the following formula was synthesized as below.
HOCH$_2$CH(OH)CH$_2$OCH$_2$CF$_2$CF$_2$O(CF$_2$CF$_2$CF$_2$O)$_d$CF$_2$CF$_2$C H$_2$—OCH$_2$CH(OH)CH$_2$OCH$_2$C(CH(CH$_3$)(CH$_3$))(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH) CH$_2$OH That is, the compound 13 is represented by the structural formula shown in FIG. 4.

41 g of the compound 13 was obtained in the same manner as in Example 1, except that 2-ethyl-2-(hydroxymethyl)-1,3-propanediol was replaced by 2-(dihydroxymethyl)-2-(3-methyl butyl)-1,3-propanediol.

The compound 13 was a transparent, pale yellow liquid having a density of 1.75 g/cm$^3$ at 20° C. Identification results of the compound 13 by NMR are as shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]
δ=−83.7 ppm [20F, —OCF$_2$CF$_2$CF$_2$O—]
δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]
δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

The results of $^{19}$F-NMR demonstrate that the compound 13 had d=5.2.

$^1$H-NMR (solvent: none, reference material: D$_2$O) δ=2.5 ppm to 5.0 ppm [41H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH(CH$_3$) (CH$_3$)) (CH$_2$OH)CH$_2$OCH$_2$CH(OH)C H$_2$O—CH$_2$CF$_2$CF$_2$O(CF$_2$CF$_2$CF$_2$O)$_d$CF$_2$CF$_2$CH$_2$OCH$_2$CH(OH)CH$_2$O H]

δ=0.5 ppm to 2.0 ppm [7H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH(CH$_3$)(CH$_3$))(CH$_2$OH)CH$_2$OCH$_2$CH(OH)C H$_2$O—CH$_2$CF$_2$CF$_2$O(CF$_2$CF$_2$CF$_2$O)$_d$CF$_2$CF$_2$CH$_2$OCH$_2$CH(OH)CH$_2$O H]

The compound 13 thus obtained was used as a lubricant of Example 13.

Example 14

A compound 14 represented by the following formula was synthesized as below.
HOCH$_2$CH(OH)CH$_2$OCH$_2$CF$_2$CF$_2$O(CF$_2$CF$_2$CF$_2$O)$_d$CF$_2$CF$_2$C H$_2$—OCH$_2$CH(OH)CH$_2$OCH$_2$C(CH$_2$C$_6$H$_5$)(CH$_2$OH)CH$_2$OCH$_2$CH(OH) CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH That is, the compound 14 is represented by the structural formula shown in FIG. 4.

60 g of the compound 14 was obtained in the same manner as in Example 1, except that 2-ethyl-2-(hydroxymethyl)-1,3-propanediol was replaced by 2-(hydroxymethyl)-2-(phenylmethyl)-1,3-propanediol.

The compound 14 was a transparent, pale yellow liquid having a density of 1.74 g/cm$^3$ at 20° C. Identification results of the compound 14 by NMR are as shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]
δ=−83.7 ppm [20F, —OCF$_2$CF$_2$CF$_2$O—]
δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]
δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

The results of $^{19}$F-NMR demonstrate that the compound 14 had d=5.3.

$^1$H-NMR (solvent: none, reference material: D$_2$O)
δ=2.5 ppm to 5.0 ppm [41H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_5$) (CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=2.8 ppm [2H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_5$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=7.4 ppm [5H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_5$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

The compound 14 thus obtained was used as a lubricant of Example 14.

Example 15

A compound 15 represented by the following formula was synthesized as below.
HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_4$NO$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH That is, the compound 15 is represented by the structural formula shown in FIG. 4.

21 g of the compound 15 was obtained in the same manner as in Example 1, except that 2-ethyl-2-(hydroxymethyl)-1,3-propanediol was replaced by 2-(hydroxymethyl)-2-[(4-nitrophenyl)methyl]-1,3-propanediol.

The compound 15 was a transparent, pale yellow liquid having a density of 1.74 g/cm$^3$ at 20° C. Identification results of the compound 15 by NMR are as shown below.

$^{19}$F-NMR (solvent: none, reference material: OCF$_2$CF$_2$CF$_2$O in the product [–129.7 ppm])
δ=–129.7 ppm [10F, —OCF$_2$CF$_2$CF$_2$O—]
δ=–83.7 ppm [20F, —OCF$_2$CF$_2$CF$_2$O—]
δ=–124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]
δ=–86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

The results of $^{19}$F-NMR demonstrate that the compound 15 had d=5.1.

$^1$H-NMR (solvent: none, reference material: D$_2$O)
δ=2.5 ppm to 5.0 ppm [41H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_4$NO$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]
δ=2.8 ppm [2H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_4$NO$_2$)(CH$_2$OH)CH$_2$OCH$_2$CH(OH)CH$_2$O—CH$_2$CF$_2$CF$_2$O(CF$_2$CF$_2$F$_2$O)$_d$CF$_2$CF$_2$CH$_2$OCH$_2$CH(OH)CH$_2$OH]
δ=7.5 ppm to 8.0 ppm [4H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_2$C$_6$H$_4$NO$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

The compound 15 thus obtained was used as a lubricant of Example 15.

Example 16

A compound 16 represented by the following formula was synthesized as below.
HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_4$NH$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH That is, the compound 16 is represented by the structural formula shown in FIG. 4.

35 g of the compound 16 was obtained in the same manner as in Example 1, except that 2-ethyl-2-(hydroxymethyl)-1,3-propanediol was replaced by 2-[(4-aminophenyl-9-methyl)-2-(hydroxymethyl)-1,3-propanediol].

The compound 16 was a transparent, pale yellow liquid having a density of 1.76 g/cm$^3$ at 20° C. Identification results of the compound 16 by NMR are as shown below.

$^{19}$F-NMR (solvent: none, reference material: OCF$_2$CF$_2$CF$_2$O in the product [–129.7 ppm])
δ=–129.7 ppm [10F, —OCF$_2$CF$_2$CF$_2$O—]
δ=–83.7 ppm [20F, —OCF$_2$CF$_2$CF$_2$O—]
δ=–124.2 ppm [8F, —OCF$_2$CF$_2$CH$_2$OCH$_2$CH(OH)CH$_2$O—, —OCF$_2$CF$_2$CH$_2$OCH$_2$CH(OH) CH$_2$OH]
δ=–86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

The results of $^{19}$F-NMR demonstrate that the compound 16 had d=5.0.

$^1$H-NMR (solvent: none, reference material: D$_2$O)
δ=2.5 ppm to 5.0 ppm [41H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_4$NH$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH)
δ=2.8 ppm [2H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$C$_6$H$_4$NH$_2$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH) CH$_2$OH]
δ=6.3 ppm to 7.4 ppm [6H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_2$C$_6$H$_4$NH$_2$) (CH$_2$OH) CH$_2$OCH$_2$CH(O H)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

The compound 16 thus obtained was used as a lubricant of Example 16.

Example 17

A compound 17 represented by the following formula was synthesized as below.
HOCH$_2$CH(OH)CH$_2$OCH$_2$CF$_2$CF$_2$O(CF$_2$CF$_2$O)$_c$CF$_2$CH$_2$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH That is, the compound 17 is represented by the structural formula shown in FIG. 4.

19 g of the compound 17 was obtained in the same manner as in Example 1, except that not only HOCH$_2$CF$_2$CF$_2$O(CF$_2$CF$_2$CF$_2$O)$_d$CF$_2$CF$_2$CH$_2$OH but also HOCH$_2$CF$_2$O(CF$_2$CF$_2$O)$_c$CF$_2$CH$_2$OH was used.

The compound 17 was a transparent, pale yellow liquid having a density of 1.74 g/cm$^3$ at 20° C. Identification results of the compound 17 by NMR are as shown below.

$^{19}$F-NMR (solvent: none, reference material: OCF$_2$CF$_2$CF$_2$O in the product [–129.7 ppm])
δ=–129.7 ppm [10F, —OCF$_2$CF$_2$CF$_2$O—]
δ=–83.7 ppm [20F, —OCF$_2$CF$_2$CF$_2$O—]
δ=–124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]
δ=–86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]
δ=–89.1 ppm [28F, —OCF$_2$CF$_2$O—]
δ=–79.0 ppm [4F, —OCF$_2$CH$_2$OCH$_2$CH(OH)CH$_2$O—, —OCH$_2$CH(OH)CH$_2$O—OCF$_2$CH$_2$OCH$_2$CH(OH)CH$_2$OH]

The results of $^{19}$F-NMR demonstrate that the compound 17 had d=5.1 and c=7.5.

$^1$H-NMR (solvent: none, reference material: D$_2$O)

δ=2.5 ppm to 5.0 ppm [41H, HOCH$_2$CH(OH)CH$_2$OCH$_2$CF$_2$O(CF$_2$CF$_2$O)$_c$CF$_2$CF$_2$CH$_2$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$C F$_2$O(CF$_2$CF$_2$CF$_2$O)$_d$ CF$_2$CF$_2$CH$_2$OCH$_2$CH(OH)CH$_2$OH]

δ=1.3 ppm [2H, HOCH$_2$CH(OH)CH$_2$OCH$_2$CF$_2$O(CF$_2$CF$_2$O)$_c$CF$_2$CH$_2$—OCH$_2$CH(OH)C H$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=0.9 ppm [3H, HOCH$_2$CH(OH)CH$_2$OCH$_2$CF$_2$O(CF$_2$CF$_2$O)$_c$CF$_2$CH$_2$—OCH$_2$CH(OH)C H$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

The compound 17 thus obtained was used as a lubricant of Example 17.

Example 18

A compound 18 represented by the following formula was synthesized as below.

CH$_3$OC$_6$H$_4$OCH$_2$CH(OH) CH$_2$OCH$_2$CF$_2$CF$_2$O(CF$_2$CF$_2$CF$_2$O)$_d$ CF$_2$CF$_2$CH$_2$—OCH$_2$CH(OH)CH$_2$OCH$_2$C(CH$_2$CH$_3$)(CH$_2$OH)CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH

That is, the compound 18 is represented by the structural formula shown in FIG. 4.

15 g of the compound 18 was obtained in the same manner as in Example 1, except that not only glycidol but also the compound (c-1) was used.

The compound 18 was a colorless, transparent liquid having a density of 1.75 g/cm$^3$ at 20° C. Identification results of the compound 1 by NMR are as shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]

δ=−83.7 ppm [20F, —OCF$_2$CF$_2$CF$_2$O—]

δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OC$_6$H$_4$OCH$_3$, —OCF$_2$CF$_2$CH$_2$OCH$_2$CH(OH)CH$_2$OH]

δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OC$_6$H$_4$OCH$_3$, —OCF$_2$CF$_2$CH$_2$OCH$_2$CH(OH)CH$_2$OH]

The results of $^{19}$F-NMR demonstrate that the compound 18 had d=5.1.

$^1$H-NMR (solvent: none, reference material: D$_2$O)

δ=2.5 ppm to 5.0 ppm [43H, CH$_3$OC$_6$H$_4$OCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$) (CH$_2$OH)CH$_2$OCH$_2$CH(O H)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=1.3 ppm [2H, CH$_3$OC$_6$H$_4$OCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH)CH$_2$OCH$_2$CH(O H)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=0.9 ppm [3H, CH$_3$OC$_6$H$_4$OCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$C(CH$_2$CH$_3$)(CH$_2$OH)CH$_2$OCH$_2$CH(O H)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

δ=6.5 ppm to 7.5 ppm [4H, —OCF$_2$CF$_2$CH$_2$OCH$_2$CH(OH)CH$_2$OC$_6$H$_4$OCH$_3$]

The compound 18 thus obtained was used as a lubricant of Example 18.

Example 19

A compound 19 represented by the following formula was synthesized as below.

HOCH$_2$CH(OH)CH$_2$OCH$_2$CF$_2$CF$_2$O(CF$_2$CF$_2$CF$_2$O)$_d$CF$_2$CF$_2$C H$_2$—OCH$_2$CH(OH)CH$_2$OCH$_2$C(CH$_2$OH)$_2$CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH

That is, the compound 19 is represented by the structural formula shown in FIG. 4.

30 g of the compound 19 was obtained in the same manner as in Example 1, except that 2-ethyl-2-(hydroxymethyl)-1,3-propanediol was replaced by 2,2-bis(hydroxymethyl)-1,3-propanediol.

The compound 19 was a colorless, transparent liquid having a density of 1.71 g/cm$^3$ at 20° C. Identification results of the compound 19 by NMR are as shown below.

$^{19}$F-NMR (solvent: none, reference material: OCF$_2$CF$_2$CF$_2$O in the product [−129.7 ppm])

δ=−129.7 ppm [10F, —OCF$_2$CF$_2$CF$_2$O—]

δ=−83.7 ppm [20F, —OCF$_2$CF$_2$CF$_2$O—]

δ=−124.2 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

δ=−86.5 ppm [8F, —OCF$_2$CF$_2$CH$_2$OCH$_2$CH(OH)CH$_2$O—, —OCF$_2$CF$_2$CH$_2$OCH$_2$CH(OH)CH$_2$OH]

The results of $^{19}$F-NMR demonstrate that the compound 19 had d=5.1.

$^1$H-NMR (solvent: none, reference material: D$_2$O)

δ=2.5 ppm to 5.0 ppm [44H, HOCH$_2$CH(OH)CH$_2$OCH$_2$CF$_2$CF$_2$O(CF$_2$CF$_2$CF$_2$O)$_d$CF$_2$CF$_2$CH$_2$—OCH$_2$CH(OH)CH$_2$OCH$_2$(CH$_2$OH)$_2$CH$_2$OCH$_2$CH(OH)CH$_2$O—CH$_2$CF$_2$CF$_2$O(CF$_2$CF$_2$CF$_2$O)$_d$CF$_2$CF$_2$CH$_2$OCH$_2$CH(OH)CH$_2$OH]

The compound 19 thus obtained was used as a lubricant of Example 19.

Example 20

A compound 20 represented by the following formula was synthesized as below.

HOCH$_2$CH(OH)CH$_2$OCH$_2$CF$_2$CF$_2$O(CF$_2$CF$_2$CF$_2$O)$_d$CF$_2$CF$_2$C H$_2$—OCH$_2$CH(OCH$_2$CH(OH)CH$_2$OH)CH$_2$O—CH$_2$CF$_2$CF$_2$O(CF$_2$CF$_2$CF$_{20}$)$_d$CF$_2$CF$_2$CH$_2$OCH$_2$CH(OH)CH$_2$OH

That is, the compound 20 is represented by the structural formula shown in FIG. 4.

In an argon atmosphere, 40 g of t-butyl alcohol, 90 g of a fluoropolyether represented by HOCH$_2$CF$_2$CF$_2$O(CF$_2$CF$_2$CF$_2$O)$_d$CF$_2$CF$_2$CH$_2$OH (number average molecular weight: 1141, molecular weight distribution: 1.24), 4.8 g of potassium t-butoxide, and 3.6 g of epichlorohydrin were stirred at 70° C. for 14 hours. Then, a resultant mixture was washed with water, dehydrated, and then purified by silica gel column chromatography. Consequently, 40 g of a linear fluoropolyether compound (average molecular weight: 2512) having a hydroxyl group in a perfluoropolyether chain was obtained. 40 g of this compound was dissolved in 20 g of t-butyl alcohol. Then, 1.0 g of potassium t-butoxide and 4.0 g of glycidol were added thereto, and the resultant was stirred at 70° C. for 15 hours. Then, the resultant was washed with water, dehydrated, and then purified by silica gel column chromatography. Consequently, 20 g of the compound 20 was obtained.

The compound 20 was a transparent, pale yellow liquid having a density of 1.78 g/cm$^3$ at 20° C. Identification results of the compound 20 by NMR are as shown below.

$^{19}$F-NMR (solvent: none, reference material: $OCF_2CF_2CF_2O$ in the product [−129.7 ppm])

δ=−129.7 ppm [10F, —$OCF_2CF_2CF_2O$—]
δ=−83.7 ppm [20F, —$OCF_2CF_2CF_2O$—]
δ=−124.2 ppm [8F, —$OCF_2CF_2CH_2OCH_2CH(OCH_2CH(OH)CH_2OH)$—$CH_2OCH_2CF_2CF_2$—, —$OCF_2CF_2CH_2OCH_2CH(OH)CH_2OH$]
δ=−86.5 ppm [8F, —$OCF_2CF_2CH_2OCH_2CH(OCH_2CH(OH)CH_2OH)$—$CH_2OCH_2CF_2CF_2$—, —$OCF_2CF_2CH_2OCH_2CH(OH)CH_2OH$]

The results of $^{19}$F-NMR demonstrate that the compound 20 had d=5.2.

$^1$H-NMR (solvent: none, reference material: $D_2O$)

δ=2.5 ppm to 5.0 ppm [34H, $HOCH_2CH(OH)CH_2OCH_2CF_2CF_2O(CF_2CF_2CF_2O)_dCF_2CF_2CH_2$—$OCH_2CH(OCH_2CH(OH)CH_2OH)CH_2O$—$CH_2CF_2CF_2O(CF_2CF_2CF_2O)_dCF_2CF_2CH_2OCH_2CH(OH)CH_2OH$]

The compound 20 thus obtained was used as a lubricant of Example 20.

Example 21

A compound 21 represented by the following formula was synthesized as below.

$HOCH_2CH(OH)CH_2OCH_2CF_2O(CF_2CF_2O)_cCF_2CH_2$—$OCH_2CH(OCH_2CH(OH)CH_2OH)CH_2O$—$CH_2CF_2O(CF_2CF_2O)CF_2CH_2OCH_2C H(OH)CH_2OH$

That is, the compound 21 is represented by the structural formula shown in FIG. 4.

21 g of the compound 21 was obtained in the same manner as in Example 20, except that a fluoropolyether represented by $HOCH_2CF_2CF_2O(CF_2CF_2CF_2O)_dCF_2CF_2CH_2OH$ was replaced by a fluoropolyether represented by $HOCH_2CF_2O(CF_2CF_2O)_cCF_2CH_2OH$.

The compound 21 was a waxy, white solid. The compound 21 had a density of 1.72 g/cm$^3$ at 20° C. Identification results of the compound 21 by NMR are as shown below.

$^{19}$F-NMR (solvent: none, reference material: $OCF_2CF_2O$ in the product [−89.1 ppm])

δ=−89.1 ppm [32F, —$OCF_2CF_2O$—]
δ=−79.0 ppm [8F, —$OCF_2CH_2OCH_2CH(OCH_2CH(OH)CH_2OH)CH_2O$—, —$OCF_2CH_2OCH_2CH(OH)CH_2OH$]

The results of $^{19}$F-NMR demonstrate that the compound 21 had c=8.9.

$^1$H-NMR (solvent: none, reference material: $D_2O$)

δ=2.5 ppm to 5.0 ppm [34H, $HOCH_2CH(OH)CH_2OCH_2CF_2O(CF_2CF_2O)_cCF_2CH_2$—$OCH_2CH(OCH_2CH(OH)CH_2OH)CH_2O$—$CH_2CF_2O(CF_2CF_2O)_cCF_2CH_2OCH_2CH(OH) CH_2OH$]

The compound 21 thus obtained was used as a lubricant of Example 21.

Comparative Example 1

As a lubricant of Comparative Example 1, a compound 22 was used. As indicated below, the compound 22 did not have a structure in which two perfluoropolyethers were bonded to each other through an aliphatic ether.

$HOCH_2CH(OH)CH_2OCH_2CF_2CF_2O(CF_2CF_2CF_2O)_dCF_2CF_2C H_2OCH_2CH(OH)CH_2OH$

That is, the compound 22 is represented by the structural formula shown in FIG. 4.

Here, d=5.1 and the molecular weight distribution was 1.20.

The compound 22 was used as a lubricant of Comparative Example 1.

Comparative Example 2

As a lubricant of Comparative Example 2, a compound 23 was used. As indicated below, the compound 23 had two perfluoropolyethers bonded to each other through an aliphatic ether having a hydroxyl group in place of a primary alcohol.

$HOCH_2CH(OH)CH_2OCH_2CF_2CF_2O(CF_2CF_2CF_2O)_dCF_2CF_2C H_2OCH_2CH(OH)CH_2OCH_2CH(OH)CH_2CH_2CH_2CH_2CH(OH)CH_2OC H_2CF_2CF_2O(CF_2CF_2CF_2O)_dCF_2CF_2CH_2OCH_2CH(OH)CH_2OH$

That is, the compound 23 is represented by the structural formula shown in FIG. 4.

Here, d=5.1 and the molecular weight distribution was 1.25.

The compound 23 was used as a lubricant of Comparative Example 2.

Comparative Example 3

As a lubricant of Comparative Example 3, a compound 24 was used. As indicated below, the compound 24 had two perfluoropolyethers bonded to each other through an aliphatic ether having a hydroxyl group, the aliphatic ether being not a primary alcohol.

$HOCH_2CH(OH)CH_2OCH_2CF_2CF_2O(CF_2CF_2CF_2O)_dCF_2CF_2C H_2OCH_2CH(OH)CH_2OCH_2CH(OH)CH_2OCH_2CH(OH)CH_2OCH_2CH(OH)CH_2OCH_2CF_2CF_2O(CF_2CF_2CF_2O)_dCF_2CF_2CH_2OCH_2CH(OH)C H_2OH$

That is, the compound 24 is represented by the structural formula shown in FIG. 4.

Here, d=5.2 and the molecular weight distribution was 1.26.

The compound 24 was used as a lubricant of Comparative Example 3.

(Results of Evaluation of Bonding Ratio)

Table 1 shows the results of measurement of the bonding ratios.

TABLE 1

|  | Ex. 1 Comp. 1 | Ex. 2 Comp. 2 | Ex. 3 Comp. 3 | Ex. 4 Comp. 4 | Ex. 5 Comp. 5 | Ex. 6 Comp. 6 |
|---|---|---|---|---|---|---|
| Bonding ratio (%) | 85 | 82 | 83 | 86 | 88 | 88 |

|  | Ex. 7 Comp. 7 | Ex. 8 Comp. 8 | Ex. 9 Comp. 9 | Ex. 10 Comp. 10 | Ex. 11 Comp. 11 | Ex. 12 Comp. 12 |
|---|---|---|---|---|---|---|
| Bonding ratio (%) | 90 | 92 | 87 | 80 | 86 | 80 |

TABLE 1-continued

| | Ex. 13 Comp. 13 | Ex. 14 Comp. 14 | Ex. 15 Comp. 15 | Ex. 16 Comp. 16 | Ex. 17 Comp. 17 | Ex. 18 Comp. 18 |
|---|---|---|---|---|---|---|
| Bonding ratio (%) | 80 | 83 | 83 | 85 | 85 | 84 |

| | Ex. 19 Comp. 19 | Ex. 20 Comp. 20 | Ex. 21 Comp. 21 | C. Ex. 1 Comp. 22 | C. Ex. 2 Comp. 23 | C. Ex. 3 Comp. 24 |
|---|---|---|---|---|---|---|
| Bonding ratio (%) | 93 | 90 | 93 | 55 | 61 | 67 |

"Ex." stands for "Example".
"Comp." stands for "Compound".
"C. Ex." stands for "Comparative Example".

Table 1 shows that the lubricant was adhered to the magnetic disk more firmly in Examples 1 to 21 than in Comparative Examples 1 to 3. This reveals that a compound in accordance with an embodiment of the present invention has excellent adhesion as a lubricant for bringing a magnetic disk into close contact with a protective layer.

INDUSTRIAL APPLICABILITY

A perfluoropolyether compound in accordance with an aspect of the present invention can suitably be used as a lubricant for magnetic disks.

REFERENCE SIGNS LIST

1: Magnetic disk
2: Lubricant layer
3: Protective film layer (protective layer)
4: Recording layer
5: Lower layer
6: Soft magnetic lower layer
7: Adhesive layer
8: Non-magnetic substrate

The invention claimed is:

1. A perfluoropolyether compound represented by the following formula (1):

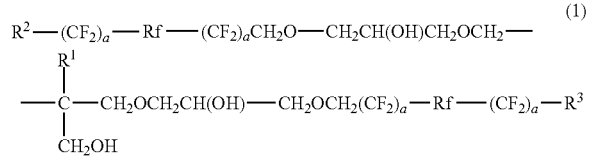

(1)

where:
a is an integer of 1 to 5;
$R^1$ is a hydrogen atom, a hydrocarbon group, or a polar group;
$R^2$ and $R^3$ are each independently —F, —$CH_2OH$, —$CH_2OCH_2CH(OH)CH_2OH$, —$CH_2OCH_2CH(OH)CH_2OCH_2CH(OH)CH_2OH$, —$CH_2O(CH_2)_gOH$, —$CH_2OCH_2CH(OH)CH_2OC_{12}E_9O$, —$CH_2OCH_2CH(OH)CH_2OC_{10}H_7$, or $CH_2OCH_2CH(OH)CH_2OC_6H_4$—$R^4$, where g is a real number of 1 to 10, and $R^4$ is a hydrogen atom, a hydroxyl group, a $C_1$-$C_4$ alkoxy group, an amino group, or an amido group; and
Rf is represented by the following formula (2):

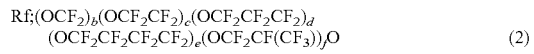

(2)

where:
b and c are each a real number of 0 to 50;
d, e, and f are each a real number of 0 to 30; and
at least one of b, c, d, e, and f is a real number of 1 or more.

2. A lubricant comprising the perfluoropolyether compound recited in claim 1.

3. A magnetic disk comprising:
a recording layer;
a protective layer disposed on the recording layer; and
a lubricant layer disposed on the protective layer,
the lubricant layer containing the lubricant recited in claim 2.

4. A perfluoropolyether compound represented by the following formula (3):

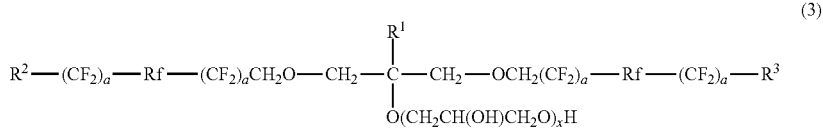

(3)

where:
a is an integer of 1 to 5 and x is a real number of 1 to 5;
$R^1$ is a hydrogen atom, a hydrocarbon group, or a polar group;
$R^2$ and $R^3$ are each independently —F, —$CH_2OH$, —$CH_2OCH_2CH(OH)CH_2OH$, —$CH_2OCH_2CH(OH)CH_2OCH_2CH(OH)CH_2OH$, —$CH_2O(CH_2)_gOH$, —$CH_2OCH_2CH(OH)CH_2OC_{12}H_9O$, —$CH_2OCH_2CH(OH)CH_2OC_{10}H_7$, or $CH_2OCH_2CH(OH)CH_2OC_6H_4$—$R^4$, where g is a real number of 1 to 10, and $R^4$ is a hydrogen atom, a hydroxyl group, a $C_1$-$C_4$ alkoxy group, an amino group, or an amido group; and
Rf is represented by the following formula (2):

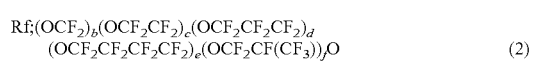

(2)

where:

b and c are each a real number of 0 to 50;

d, e, and f are each a real number of 0 to 30; and at least one of b, c, d, e, and f is a real number of 1 or more.

5. A lubricant comprising the perfluoropolyether compound recited in claim 4.

6. A magnetic disk comprising:

a recording layer;

a protective layer disposed on the recording layer; and a lubricant layer disposed on the protective layer, the lubricant layer containing the lubricant recited in claim 5.

* * * * *